United States Patent [19]

Stahl et al.

[11] Patent Number: 5,470,843
[45] Date of Patent: Nov. 28, 1995

[54] CARBOHYDRATE-CONTAINING POLYMERS, THEIR PREPARATION AND USE

[75] Inventors: Wilhelm Stahl, Frankfurt am Main; Michael Ahlers, Mainz; Axel Walch, Frankfurt am Main; Eckhart Bartnik, Wiesbaden; Gerhard Kretzschmar, Eschborn; Susanne Grabley, Koenigstein; Rudolf Schleyerbach, Hofheim/Taunus, all of Germany

[73] Assignee: Hoechst Aktiengesellschaft, Germany

[21] Appl. No.: 165,805

[22] Filed: Dec. 13, 1993

[30] Foreign Application Priority Data

Dec. 11, 1992 [DE] Germany .......................... 42 41 829.1
Aug. 10, 1993 [DE] Germany .......................... 43 26 777.7

[51] Int. Cl.⁶ .................................................. A61K 31/735
[52] U.S. Cl. .............................. 514/61; 525/32.2; 514/25; 514/54; 514/55; 514/56; 514/60; 536/4.1; 536/20; 536/21; 536/17.2; 536/18.5; 536/18.7; 536/45; 536/102; 536/124
[58] Field of Search ....................... 536/20, 21, 102, 536/4.1, 17.2, 18.7, 45, 18.5, 124; 514/25, 54, 55, 56, 60, 61; 525/32.2

[56] References Cited

U.S. PATENT DOCUMENTS

| 4,804,542 | 2/1989 | Fischer et al. | 424/456 |
| 5,059,654 | 10/1991 | Hou et al. | 525/54.1 |
| 5,219,926 | 6/1993 | Lindman et al. | 525/54.1 |

FOREIGN PATENT DOCUMENTS

| 0089938 | 9/1983 | European Pat. Off. . |
| 0089939 | 9/1983 | European Pat. Off. . |
| 0089940 | 9/1983 | European Pat. Off. . |
| 92/02527 | 2/1992 | WIPO . |
| 92/07006 | 4/1992 | WIPO . |

OTHER PUBLICATIONS

Ahlers et al. *Adv. Mater.* 1992, 4(3), 230–234.
Spaltenstein et al. *J. Am. Chem. Soc.* 1991, 113, 686–687.
Rathi et al. *J. Polym. Sci. A: Polym. Chem.* 1991, 29, 1895–1902.
Nishimura et al. *Macromolecules* 1991, 24, 4236–4241.

*Primary Examiner*—Douglas W. Robinson
*Assistant Examiner*—Kathleen Kahler Fonda
*Attorney, Agent, or Firm*—Foley & Lardner

[57] ABSTRACT

Carbohydrate-containing polymers which can have an HLB* of from about 10 to about 20 are disclosed. The compounds comprise a hydrophilic polymer portion, a carbohydrate portion comprising from 1 to about 20 naturally occurring, identical or different, monosaccharide units, at least one bifunctional spacer coupling the carbohydrate portion to the hydrophilic polymer portion, and a potentiator moiety. The potentiator moiety can be is a crosslinking moiety located within the hydrophilic polymer or a hydrophobic, hydrophilic or ionic moiety. Processes for the preparation and use of such polymers are also disclosed.

14 Claims, No Drawings

CARBOHYDRATE-CONTAINING POLYMERS, THEIR PREPARATION AND USE

FIELD OF THE INVENTION

The invention relates to carbohydrate-containing polymers. Processes for the preparation of such polymers and their uses are also part of the invention.

BACKGROUND OF THE INVENTION

The importance of carbohydrates in biologically-relevant recognition processes has only recently come to light. T. Feizi, *Biochem. J.* 245:1 (1987); Stults et al., *Meth. Enzym.* 179:167 (1989); S. Hakamori, *Adv. Cancer Res.* 52:257 (1989); Bevilacqua et al., *Science* 243:1160 (1989). These demonstrate that carbohydrates, along with proteins and nucleic acids, act as primary biologic information carriers.

The capability of carbohydrates to store and communicate information results largely from their complex stereochemistry. The multitude of stereocenters present in even small carbohydrates permits information storage analogous to that encoded in nucleic acids and in proteins. Moreover, the exposure of many carbohydrates on cell surfaces makes it possible for them to play a role in intercellular communication and recognition processes, largely on the basis of receptor-ligand interactions. Carbohydrates may be distinct macromolecules but usually are attached to other moieties such as lipids or proteins.

Examples of ligands which bind to membrane-bound receptor molecules are protein hormones and growth factors. Following binding of the cell surface receptor by the ligand, a signal is transferred to the cell interior which induces changes in the metabolism of the cell. After a certain period of time, the receptor-ligand complex is metabolically degraded and cellular metabolism returns to normal. For a review on this topic, see Alberts et al., *MOLECULAR BIOLOGY OF THE CELL*, 3rd edition, Garland Publishing Inc., New York, USA, page 733.

Carbohydrates on the surfaces of mammalian cells also serve as recognition domains for pathogenic agents. See, for example, J. C. Paulson, *THE RECEPTORS*, Vol. II, P. M. Conn (ed., Academic Pres (1985), page 131 (viruses); Strömberg et al., *EMBO J.* 9:2001 (1990) (bacteria); Karlsson et al., *SOURCEBOOK OF BACTERIAL PROTEIN TOXINS*, Alouf and Freer (ed.), Academic Press (1991), page 435 (toxins); Michel et al., *Appl. Environ. Microbiol.* 56:3537 (1990) (lectins). Thus, it is clear that carbohydrates play an important role in diseases which require an initial recognition of cell surface determinants.

For example, the first step in viral infection is the attachment of the virus to a host cell. This involves the specific binding viral surface proteins to receptors on the host cell membrane. These viral proteins generally are glycoproteins with a receptor binding function. Next, all or part of the viral particle is taken up into the cell and, by a complex mechanism, the viral genome is uncoated and replication proceeds.

Receptor-ligand complexes also play a part in inflammatory processes. Bradley et al., *Cell* 63:861 (1990). Investigations have shown, for example, that the protein ELAM 1, which is synthesized and expressed by endothelial cells in vivo, probably mediates the adhesion of leukocytes to the inflammatory focus.

The use of free oligosaccharides to diagnose and combat bacterial, viral and inflammatory disorders by competing for binding of natural ligands to the above-described receptors, has been impeded by the low affinity between receptors and the corresponding oligosaccharide ligands. Because of this low affinity, massive amounts of a competing carbohydrate are required to effectively block binding of the corresponding ligand, necessary both for diagnosis and therapy. Connolly et al., *J. Biol. Chem.* 257:939 (1982) ($K_D$=~$10^{-4}$M for the interaction between a monovalent galactoside and the corresponding lectin).

By coupling a plurality of ligands to a "surface," an increased interaction between the receptor and ligand theoretically can be achieved. For example, the influenza virus hemagglutinin, which binds to neuraminic acid on the cell surface, has a greater affinity for its receptor when a polyvalent structure is presented. Spaltenstein et al., *J. Am. Chem. Soc.* 113:686 (1991) (monovalent: $K_D$=$2\times10^{-4}$M; polyvalent: $K_D$=$3\times10^{-7}$M).

To date, a number of different "surfaces" have been investigated for their use in generating polyvalent structures, all of which have drawbacks: (a) liposomes—N. Yamazaki, *Int. J. Biochem.* 24:99 (1992); (b) polyacrylamides; (c) polylysines; and (d) sulfated polysaccharides. Each of these "surfaces" is discussed below.

Liposomes may be obtained from cell preparations or prepared from synthetic lipids. A ligand such as a carbohydrate can be held on the liposome surface by means of hydrophobic alkyl radical, attached at one point to the carbohydrate. The hydrophobic radical will be embedded in the hydrophobic membrane of the liposome, thus anchoring the complex. The disadvantages of using liposomes for this purposes are their low stability and half-life in vivo. Liposome preparations, along with other oligomeric and polymeric "surfaces" are described in WO 91/19501 and WO 91/19502.

Polyacrylamide-based polymers, prepared by polymerization of carbohydrate-containing monomers, are generally considered unsuitable as carriers of ligands for medical use. See, for example, Rathi et al., *J. Polym. Sci.* 29:1985 (1991) (polymerization of carbohydrate-containing acrylamide monomers for use as carrier of active substances); Nishimura et al., *Macromolecules* 24:4236 (1991) (copolymerized pentylglycosides with acrylamide and investigate the interaction of this macromolecule with lectins). Because the polymer portion of these compounds is composed entirely of C—C bonds, however, a crucial disadvantage arises for in vivo diagnostic and therapeutic use in that these polyacrylamide bonds are degraded in vivo to toxic metabolites and thus are not well tolerated by the subject. The relatively hydrophobic nature of these polymers also may result in unfavorable presentation of the receptor binding portion of the molecule. Moreover, both Rathi et al. and Nishimura et al. use the polymer only as carrier for a carbohydrate moiety and a pharmacologically active macromolecule.

Polylysine is composed of physiologically tolerated units. The disadvantage of polylysine, however, is in the large number of free $NH_2$ groups which cause non-specific interactions with cells or cell surface structures. Because of the spurious interactions, it normally is impossible to achieve a site-specific effect using polylysine-containing compounds.

Conventional sulfated polysaccharides can offer only ionic interactions of low specificity. There apparently is non-specific adhesion of these compounds to any available cell surfaces and, therefore, they can offer no specific receptor blocking functions.

The interactions of dextran-fixed β-blockers with β-adrenoreceptors have been investigated. Pitka and Kusiak, in "Macromolecules as Drugs and as Carriers for Biologically Active Material", Tirell, Donaruma and Turek (ed.), *The New York Academy of Sciences* 446:249 (1985). β-blockers are artificial active substances which, in this report, were linked via a spacer to the polysaccharide carrier dextran. Blocking of the β-adrenoreceptors took place not by a specific receptor-ligand binding, however, but by a comparatively non-specific attachment of the blocker to the receptor.

EPA 0 089 938, EPA 0 089 939 and EPA 0 089 940 disclose sugar compounds of various chain lengths which are identical to ligands located on cell surfaces or receptors located on macroorganisms. The thrust of these applications is to use sugar compounds to bind receptors located on pathogenic microorganisms in vitro and in vivo. Thus, the diagnosis and treatment of mammalian disorders, especially those of a bacterial or viral nature are contemplated. Examples are provided for the in vitro diagnosis of bacterial infections but not for in vivo diagnosis or therapy. Also discussed are sugar compounds, coupled to a carrier either directly or via spacers, for use in preparation of antibodies, isolation of cell surface structures and disinfection of wounds. These compounds are monovalent and associate with receptors in a relatively random fashion. Thus, the binding affinities of the blockers are relatively low.

WO 92/02527 discloses macromolecules which are composed of a physiologically inert "solid carrier" and saccharide units and function as ligands for the ELAM-1 receptor. These macromolecules are suggested as useful in diagnosis of inflammatory processes in vitro but not in vivo. These compounds tend to have solubility problems, however, which limits their ability to bind the cognate receptor.

Besides toxicity and non-specific interactions, another problem with many prior art polymer "surfaces" is their relatively poor solubility. Hence, the improved binding affinity achieved by rendering carbohydrates polyvalent may be negated. Additionally, low flexibility or high steric hindrance, often associated with polymers, can decrease the binding affinity of the carbohydrate moieties.

SUMMARY OF THE INVENTION

Therefore, an object of the present invention is to provide carbohydrate-containing polymers.

Another object of the present invention is to provide a process of the synthesis of such carbohydrate-containing polymers.

In satisfying the foregoing objectives, there is provided a carbohydrate-containing polymer which can have an HLB* of from about 10 to about 20, preferably 14–20. The compound comprises a hydrophilic polymer portion, a carbohydrate portion comprising from 1 to about 20 naturally occurring, identical or different, monosaccharide units, preferably 1–15 and most preferably 1–10 of such units, at least one bifunctional spacer coupling the carbohydrate portion to the hydrophilic polymer portion, and a potentiator moiety. The individual components of the compound can be linked enzymatically, chemically and/or chemoenzymatically.

Advantageously, the potentiator moiety can be a crosslinking moiety located within the hydrophilic polymer or a hydrophobic, hydrophilic or ionic moiety that alters the charge structure or solubility of the hydrophilic polymer.

In another embodiment, there is provided a pharmaceutical composition comprising the compound described above.

In another embodiment, there is provided a process for preparing the compound described above.

In another embodiment, there is provided a method of treating bacterial, viral and inflammatory disease employing the compound described above.

In another embodiment, there is provided a method for improving the receptor binding affinity of a polymer which comprises a carbohydrate group comprising covalently linking said polymer to a potentiator selected from the group consisting of a (i) a crosslinking moiety within said hydrophilic polymer;
(ii) a hydrophobic or ionic moiety, wherein presentation of the portion of said carbohydrate-containing polymer that interacts with a cognate receptor is enhanced such that the binding affinity of the carbohydrate-containing molecule for said cognate receptor is increased or the solubility of said carbohydrate-containing polymer is increased.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

As discussed above, the use of carbohydrate compounds to diagnose and treat bacterial, viral and inflammatory disorders is a desired goal but steps toward achieving that goal have been limited by the relatively low affinity of the prior art compounds for cognate receptors. The carbohydrate-containing polymers according to the present invention, however, are characterized by a relatively high affinity for certain biological receptors. This results, in general, from their ability to present to the receptor a ligand capable of binding with that receptor without interfering effects from other regions of the molecule. This is achieved by presenting the carbohydrate-containing polymer to the receptor in a distended form, a phenomenon brought about by the addition of a potentiator molecule which (i) increases the rigidity of the polymer and, hence, reduces the tendency of the carbohydrate portions of the molecule to fold in upon one another (ii) increases the solubility of the molecule as a whole or (iii) alters the electrostatic character of the carbohydrate-containing polymer such that interaction with cognate receptor is improved.

Compounds according to the present invention are useful in a variety of different applications including in vitro, in situ and in vivo diagnosis of various pathological states such as infectious and inflammatory diseases. In addition, these compounds may be used to treat patients in vivo for the same pathological states described above.

One type of potentiator is a crosslinking moiety that is attached, at two separate locations, to the polymer. The crosslinking moiety provides rigidity and spatial separation of the polymer. Thus, this polymer remains in a distended form, as compared to polymers that lack potentiator portions. Because of this improved conformation, the binding portions of the molecule are better able to interact with their cognate receptors and, hence, a higher binding affinity results with ultimate benefit of better receptor blocking activity.

A second type of potentiator is a hydrophobic, hydrophilic or ionic moiety. Depending on the particular receptor to be targeted, it may be desirable to create different electrostatic charges within the carbohydrate-containing polymer, thereby maximizing the electrostatic interactions between the carbohydrate-containing polymer and the receptor. Alternatively, these moieties enhance the solubility of the carbohydrate-containing polymer. As a result of this improved solubility, the polymer tends to remain in an extended form and, thus, interactions of the binding portions of the molecule with the receptor are improved. This improved interaction increases the binding affinities of the molecule and result in a higher blocking activity than corresponding molecules with lower solubility.

In addition, carbohydrate-containing polymers of the present invention are non-toxic. More advantageously, they are cleared from the subject without causing toxic effects. Some prior art compounds, even though non-toxic in their entirety, are toxic in the form of their breakdown products. This has presented a major hurdle in extending the use of carbohydrate-containing polymers to in vivo applications. Advantageously, according to one aspect of this invention, the carbohydrate-containing polymers exhibit (i) little or no accumulation in the body, (ii) satisfactory solubility, conformation and charge and (iii) nontoxicity, even in the form of its breakdown products. The carbohydrate-containing polymer also can be used diagnostically and/or therapeutically by virtue of its ability to bind to carbohydrate receptors.

Another feature of polymers according to the present invention is that they exert their function as entire molecules and not on the basis of the activity of substructures or breakdown products. In other words, the blocking activity is found only in the complete carbohydrate-spacer-polymer-potentiator form. Unlike other carbohydrate-containing compounds in which only certain parts are the molecule contribute the blocking activity, polymer, spacer, carbohydrates and potentiator of the present compounds all contribute to the ligand structure.

Together, these qualities combine to define a genus of molecules which provide advantages over carbohydrate-containing polymers of the prior art. The remainder of the specification seeks to describe the particular components of the compounds of this invention, the uses of the compounds. Protocols also are provided for quickly screening such compounds for in vitro and in vivo applications. The following definitions are provided for certain terms used in this specification.

DEFINITIONS

Physiologically tolerated—The compound and its breakdown products are tolerated in vivo and do not cause hemolytic, antigenic or thrombogenic effects. In addition, non-specific binding to molecules such as, for example, receptors, cell membrane components, and hormones are undesired because they often lead to intolerance reactions. The use of a spacer which, in and of itself, causes intolerance reactions is possible if the molecule, in its entirety or degradation products thereof, are physiologically tolerated.

Physiologically degradable—The carbohydrate— containing polymer should be excretable in its entirety or degradable in vivo to smaller, physiologically-tolerated units in order to be, in effect, biodegradable. This applies in particular to the polymer alone. The residence time of the carbohydrate-containing polymer on the particular receptor, and thus the duration of the effect of the carbohydrate-containing polymer, is controlled via its rate of degradation. Thus, degradation would be purposely altered by the choice of, for example, the polymer units and their linkage. In this way, it would be possible to prevent accumulation of the polymer in the body.

Receptor—A receptor is a macromolecule on a membrane surface which, by reason of its charge and/or configuration, displays a site for the specific binding of one or more signal substances. Normally, a receptor recognizes only a single, natural molecule.

Ligand—A signal substance which binds a receptor is a ligand. By specific binding of the ligand to the receptor, transfer of information into the cell, and subsequent alteration in cellular metabolism, is achieved.

HLB*—The hydrophilicity of the carbohydrate-containing polymer according to the invention is characterized by the HLB*. The HLB* defines the ratio of the hydrophilic and hydrophobic portions of a molecule using a scale from 1 to 20, with 1 being the most hydrophobic and 20 the most hydrophilic. See R. Heusch, *KOLLOID-ZEITSCHRIFT UND ZEITSCHRIFT FÜR POLYMERE,* Vol. 236(1):31 et seq (1970). Advantageously, the HLB* of the carbohydrate-containing polymer according to the invention is from about 10 to about 20, more advantageously from about 14 to about 20.

Oligosaccharides are sugars composed of up to about 20 naturally-occurring monosaccharide units.

Degree of loading of the polymer with the carbohydrate portion via spacer—The degree of loading indicates the percentage of the repeating units of the polymer to which the carbohydrate portion is linked via spacers. The percentage is based on the total number of repeating units. Repeating units mean the smallest regularly recurring unit which completely describes the degradation of a chain. *See MAKROMOLEKÜLE, Vol.* 1, 5th edition, Hüthig & Wepf Verlag, Basle, Heidelberg, New York (1990).

Hydrophilic, hydrophobic or ionic group according to the present invention is any compound capable of altering the electrostatic character of the molecule to which it is attached. In this context, such compounds would be selected on the basis of the electrostatic character of a given receptor and the corresponding need to alter the electrostatic character of the carbohydrate-containing polymer. In addition, hydrophilic or ionic groups that enhance the solubility of the carbohydrate-containing compounds also are desirable.

THE HYDROPHILIC POLYMER

The polymer portion of the compounds of this invention are comprised of at least two identical or different monomer units which are linked together in a linear or branched fashion, in the form of a ring (for example macrocycles), in the form of a star (dendrimers) or in the form of a ball (e.g., fullerenes), and may exhibit heterogeneity in molecular weight. Because the compounds of this invention are hydrophilic to at least some degree, the polymer portion should be hydrophilic to at least some degree. Skilled artisans readily will recognize a multitude of hydrophilic polymers which may be used with this invention.

Where a compound of this invention is to be used in vivo, it should be biodegradable, physiologically tolerated and physiologically degradable. In such cases, the polymer must meet a number of requirements in order to be physiologically tolerated. Namely, it must (i) induce no immune response in subjects in which it is to be used and (ii) avoid non-specific interactions and accumulation in the reticuloendothelial system (RES).

Polymers suitable for in vivo use include polyamides, polycarbonates, polyiminocarbonates, polyanhydrides, polyorthoesters, polyesters, polydioxanones, polyhydroxycarboxylic acids, polyaminoacids, polyphosphazenes and polysaccharides. Preferred polymers include a polyaminoacid, a polyhydroxy-carboxylic acid linked as polyester, polyamide or anhydride, or a polysaccharide preferably having a molecular weight of up to about 70 kD. The polymer preferably has a molecular weight of at least about 2 kd in order to achieve a sufficient half-life in the blood.

Suitable polymers which are particularly preferred for in vivo use include polyaspartate-amides, polysuccinimides, polyglutamates and polylysine-fumaramides belonging to the polyamino-acids, the functional polyhydroxycarboxylic acids which belong to the polyhydroxycarboxylic acids and are based on malic acid, tartaric acid or citric acid in the form of their polyesters, polyamides or polyanhydrides, as well as substituted chitosans, heparins, hyaluronic acids or starch derivatives. Skilled artisans readily will recognize other suitable polymers.

The degree of loading of the polymer with the carbohydrate portion (via spacer) is generally between about 0.5 and about 50%, preferably from about 2 to about 25%. The degree of loading varies depending on the desired function. The polymer may carry a plurality of carbohydrate moieties coupled via spacers or it may carry only a single, spacer-linked carbohydrate portion. The carbohydrate portions may be identical or they may be different. The absolute number of carbohydrate or spacer-carbohydrate moieties carried on the polymer also will vary depending on the particular carbohydrate and the intended use. Moreover, it may be advantageous, to link a plurality of the carbohydrate-containing polymers together.

CARBOHYDRATE PORTION

Carbohydrates are defined as all compounds which have a structure corresponding to the formula $C_n(H_2O)_n$, as well as polyhydroxyaldehydes, ketones, acids and amines and their naturally-occurring derivatives.

The carbohydrate portion of the claimed molecules is composed of 1–20 naturally-occurring monosaccharide units. Preferred are structures using 1–15 naturally-occurring monosaccharide units and most preferred are those using 1–10 units.

Naturally-occurring monosaccharide units are known to the skilled worker from standard organic chemistry or biochemistry texts. Beyer/Walter, *LEHRBUCH DER ORGANISCHEN CHEMIE* (Textbook of Organic Chemistry) S. Hirzel Verlag, Stuttgart, 19th edition, pages 393 et seq.; Albert L. Lehninger, *BIOCHEMISTRY*, 2nd edition, Worth Publishing Inc., New York, pages 249 et seq.; Lubert Stryer, *BIOCHEMIE* (Biochemistry), Spektrum-der-Wissenschaft-Verlagsgesellschaft GmbH, Heidelberg, Germany, 1st edition, pages 345 et seq.

Examples of monosaccharide units are the D and L configurations of aldoses are glyceraldehyde, erythrose, threose, ribose, arabinose, xylose, lyxose, allose, altrose, glucose, mannose, gulose, idose, galactose and talose and of ketoses dihydroxyacetone, erythrulose, ribulose, xylulose, puscose, fructose, sorbose and/or tagatose.

The term "naturally-occurring" monosaccharide units also includes those monosaccharides which represent naturally-occurring substitutions of the stated examples. The skilled worker understands this to mean, preferably, deoxy sugars, very preferably 2-, 3-, 4- or 6-deoxyaldoses such as, for example, focuse, rhamnose, digitoxose and most preferably 2-, 3-, 5-, 6-deoxyketoses, preferably deoxyamino sugars such as, for example, glucosamine, mannosamine, galactosamine, preferably deoxyacylamino sugars such as, for example, N-acetylglucosamine, N-acetylmannosamine, N-acetylgalactosamine, preferably aldonic, aldaric and/or uronic acids such as, for example, gluconic acid or glucuronic acid. It also is possible to use ascorbic acid, amino acid-carrying monosaccharides and monosaccharides which carry lipid, phosphatidyl or polyol residues.

The skilled worker also understands "naturally-occurring," substituted monosaccharides to mean those with a carbon chain longer than 6 carbons, as well as representatives thereof substituted in accordance with the criteria detailed above, such as, for example, ketodeoxyoctonic acid, ketodeoxynononic acid, N-acylneuraminic acids, N-acetylmuramic acid.

Preferred carbohydrate portions are those which occur on cell surfaces as components of glycoproteins, glycolipids or proteoglycans, as well as any desired segments thereof. Particularly preferred carbohydrate portions are those composed of monosaccharides which also occur in the human body, such as glucose, N-acetylglucosamine, galactose, N-acetylgalactosamine, mannose, focose, N-acetylneuraminic acid and glucuronic acid.

The monosaccharide units forming the carbohydrate portion may be identical or different. In addition, the stereochemistry of the glycosidic linkage (axial or equatorial, or α or β) of the individual monosaccharide units may be identical or different.

The complete carbohydrate portion can be composed, for example, of the following sugar residues:

Galβ1–4GlcNAc—;
Galβ1–3GlcNAc—;
SAα2–6Galβ1–4GlcNAc—;
SAα2–3Galβ1–4GlcNAc—;
SAα2–3Galβ1–3GlcNAc—;
Galβ1–4(Fucα1–3)GlcNAc—;
Galβ1–3(Fucα1–3)GlcNAc—;
SAα2–3Galβ1–3(Fucα1–4)GlcNAc—;
SAα2–3Galβ1–4(Fucα1–3)GlcNAc—;
Galβ1–4GlcNAcβ1–4GlcNAc—;
Galβ1–3GlcNAcβ1–4GlcNAc—;
SAα2–6Galβ1–4GlcNAcβ1–4GlcNAc—;
SAα2–3Galβ1–4GlcNAcβ1–4GlcNAc—;
SAα2–3Galβ1–3GlcNAcβ1–4GlcNAc—;
Galβ1–4(Fucα1–3)GlcNAcβ1–4GlcNAc—;
Galβ1–3(Fucα1–4)GlcNAcβ1–4GlcNAc—;
SAα2–3Galβ1–3(Fucα1–4)GlcNAcβ1–4GlcNAc—;
SAα2–3Galβ1–4(Fucα1–3)GlcNAcβ1–4GlcNAc—;
SAα2–3Galβ1–3(Fucα1–4)GlcNAcβ1–4Gal—;
SAα2–3Galβ1–4(Fucα1–3)GlcNAcβ1–4Gal—;
SAα2–3Galβ1–4GlcNAcβ1–3Galβ1–4(Fucα1–3)GlcNAc;
SAα2–6Galβ1–4GlcNAcβ1–3Galβ1–4(Fucα1–3)GlcNAc;
SAα2–3Galβ1–4(Fucα1–3)GlcNAcβ1–3Galβ1–4Glc;
SAα2–6Galβ1–4(Fucα1–3)GlcNAcβ1–3Galβ1–4Glc;
SAα2–3Galβ1–4GlcNAcβ1–3Galβ1–4(Fucα1–3)GlcNAcβ1–3Galβ1–4Glc;
SAα2–6Galβ1–4GlcNAcβ1–3Galβ1–4(Fucα1–3)GlcNAcβ1–3Galβ1–4Glc;
SAα2–3Galβ1–4(Fucα1–3)GlcNAcβ1–3Galβ1–4(Fucα1–3)GlcNAcβ1–3Galβ1–4Glc;
SAα2–6Galβ1–4(Fucα1–3)GlcNAcβ1–3Galβ1–4(Fucα1–3)GlcNAcβ1–3Galβ1–4Glc;

SAα2–3Galβ1–4(Fucα1–3)GlcNAcβ1–3Galβ1–4(Fucα1–3)Glc;
SAα2–6Galβ1–4(Fucα1–3)GlcNAcβ1–3Galβ1–4(Fucα1–3)Glc;
SAα2–3Galβ1–4GlcNAcβ1–3Galβ1–4(Fucα1–3)-GlcNAcβ1–3Galβ 1–4(Fucα1–3)Glc;
SAα2–6Galβ1–4GlcNAcβ1–3Galβ1–4(Fucα1–3)-GlcNAcβ1–3Galβ 1–4(Fucα1–3)Glc;
SAα2–3Galβ1–4(Fucα1–3)GlcNAcβ1–3Galβ1–4=(Fucα1–3)GlcNAcβ 1–3Galβ1–4(Fucα1–3)Glc;
SAα2–6Galβ1–4(Fucα1–3)GlcNAcβ1–3Galβ1–4-(Fucα1–3)GlcNAcβ 1–3Galβ1–4(Fucα1–3)Glc;
SAα2–3Galβ1–3(Fucα1–4)GlcNAc;
SAα2–6Galβ1–3(Fucα1–4)GlcNAc;
SAα2–3Galβ1–3GlcNAcβ1–4Galβ1–4(Fucα1–3)GlcNAc;
SAα2–6Galβ1–3GlcNAcβ1–4Galβ1–4(Fucα1–3)GlcNAc;
SAα2–3Galβ1–3(Fucα1–4)GlcNAcβ1–3Galβ1–4-(Fucα1–3)GlcNAc;
SAα2–6Galβ1–3(Fucα1–4)GlcNAcβ1–3Galβ1–4-(Fucα1–3)GlcNAc;
SAα2–3Galβ1–3(Fucα1–4)GlcNAcβ1–3Galβ1–4Glc;
SAα2–6Galβ1–3(Fucα1–4)GlcNAcβ1–3Galβ1–4Glc;
SAα2–3Galβ1–3GlcNAcβ1–4Galβ1–4(Fucα1–3)-GlcNAcβ1–3Galβ 1–4Glc;
SAα2–6Galβ1–3GlcNAcβ1–4Galβ1–4(Fucα1–3)-GlcNAcβ1–3Galβ 1–4Glc;
SAβ2–3Galβ1–3(Fucα1–4)GlcNAcβ1–3Galβ1–4--(Fucα1–3)GlcNAcβ 1–3Galβ1–4Glc;
SAα2–6Galβ1–3(Fucα1–4)GlcNAcβ1–3Galβ1–4-(Fucα1–3)GlcNAcβ 1–3Galβ1–4Glc;
SAα2–3Galβ1–3(Fucα1–4)GlcNAcβ1–3Galβ1–4-(Fucα1–3)Glc;
SAα2–6Galβ1–3(Fucα1–4)GlcNAcβ1–3Galβ1–4-(Fucα1–3)Glc;
SAα2–3Galβ1–3GlcNAcβ1–4Galβ1–4(Fucα1–3)-GlcNAcβ1–3Galβ 1–4(Fucα1–3)Glc;
SAα2–6Galβ1–3GlcNAcβ1–4Galβ1–4(Fucα1–3)-GlcNAcβ1–3Galβ 1–4(Fucα1–3)Glc;
SAα2–3Galβ1–3(Fucα1–4)GlcNAcβ1–3Galβ1–4-(Fucα1–3)GlcNAcβ 1–3Galβ1–4(Fucα1–3)Glc;
SAα2–6Galβ1–3(Fucα1–4)GlcNAcβ1–3Galβ1–4-(Fucα1–3)GlcNAcβ 1–3Galβ1–4(Fucα1–3)Glc;
SA2–3Galβ1–4GlcNAcβ1–3Galβ1–3(Fucα1–4)GlcNAc;
SA2–6Galβ1–4GlcNAcβ1–3Galβ1–3(Fucα1–4)GlcNAc;
SA2–3Galβ1–4(Fucα1–3)GlcNAcβ1–3Galβ1–3-(Fucα1–4)GlcNAc;
SA2–6Galβ1–4(Fucα1–3)GlcNAcβ1–3Galβ1–3-(Fucα1–4)GlcNAc;
SAα2–3Galβ1–4GlcNAcβ1–3Galβ1–3(Fucα1–4)-GlcNAcβ1–3Galβ 1–4Glc;
SAα2–6Galβ1–4GlcNAcβ1–3Galβ1–3(Fucα1–4)-GlcNAcβ1–3Galβ 1–4Glc;
SAα2–3Galβ1–4(Fucα1–3)GlcNAcβ1–3Galβ1–3-(Fucα1–4)GlcNAcβ 1–3Galβ1–4Glc;
SAα2–6Galβ1–4(Fucα1–3)GlcNAcβ1–3Galβ1–3-(Fucα1–4)GlcNAcβ 1–3Galβ1–4Glc;
SAα2–3Galβ1–4(Fucα1–3)GlcNAcβ1–3Galβ1–3-(Fucα1–4)Glc;
SAα2–6Galβ1–4(Fucα1–3)GlcNAcβ1–3Galβ1–3-(Fucα1–4)Glc;
SAα2–3Galβ1–4GlcNAcβ1–3Galβ1–3(Fucα1–4)-GlcNAcβ1–3Galβ 1–4(Fucα1–3)Glc;
SAα2–6Galβ1–4GlcNAcβ1–3Galβ1–3(Fucα1–4)-GlcNAcβ1–3Galβ 1–4(Fucα1–3)Glc;
SAα2–3Galβ1–4(Fucα1–3)GlcNAcβ1–3Galβ1–3-(Fucα1–4)GlcNAcβ 1–3 Galβ1–4(Fucα1–3)Glc;
SAα2–6Galβ1–4(Fucα1–3)GlcNAcβ1–3Galβ1–3-(Fucα1–4)GlcNAcβ 1–3 Galβ1–4(Fucα1–3)Glc.

[GlcNAcβ-1–3Galβ1–4]$_n$GlcNAc—, where n is a number from the series from 1 to 8;
[GlcNAcβ1–3Galβ1–4]$_n$GlcNAcβ1–4GlcNAc—, where n is a number from the series from 1 to 8;
Galβ1–4[GlcNAcβ1–3Galβ1–4]$_n$GlcNAc—, where n is a number from the series from 1 to 8;
Galβ1–3[GlcNAcβ1–3Galβ1–4]$_n$GlcNAc—, where n is a number from the series from 1 to 8;
SAα2–6Galβ1–4[GlcNAcβ1–3Galβ1–4]$_n$GlcNAc—, where n is a number from the series from 1 to 8;
SAα2–3Galβ1–4[GlcNAcβ1–3Galβ1–4]$_n$GlcNAc—, where n is a number from the series from 1 to 8;
SAα2–3Galβ1–3[GlcNAcβ1–3Galβ1–4]$_n$GlcNAc—, where n is a number from the series from 1 to 4;
Galβ1–4(Fucα1–3)GlcNAcβ1–3[Galβ1–4(Fucα1–3)$_m$—GlcNAcβ 1–3]$_n$—Galβ1–4GlcNAc—, where m is a number from the series from 0 to 1 and where n is a number from the series from 1 to 4;
Galβ1–3(Fucα1–4)GlcNAcβ1–3[Galβ1–4(Fucα1–3)$_m$—GlcNAcβ 1–3]$_n$—Galβ1–4GlcNAc—, where m is a number from the series from 0 to 1 and where n is a number from the series from 1 to 8;
SAα2–3Galβ1–3(Fucα1–4)GlcNAcβ1–3[Galβ1–4GlcNAcβ-3]$_n$— Galβ1–4GlcNA—, where n is a number from the series from 1 to 8;
SAα2–3Galβ1–4(Fucα1–3)GlcNAcβ1–3[Galβ1–4(Fucα1–3)$_m$—Glc—NAcβ1–3]$_n$—Galβ1–4GlcNAc—, where m is a number from the series from 0 to 1 and where n is a number from the series from 1 to 2;
Galβ1–4[GlcNAcβ1–3Galβ1–4]$_n$GlcNAcβ1–4GlcNAc—, where n is a number from the series from 1 to 8;
Galβ1–3[GlcNAcβ1–3Galβ1–4]$_n$GlcNAcβ1–4GlcNAc—, where n is a number from the series from 1 to 8;
SAα2–6Galβ1–4[GlcNAcβ1–3Galβ1–4]$_n$GlcNAcβ1–4GlcNAc—, where n is a number from the series from 1 to 8;
SAα2–3Galβ1–4[GlcNAcβ1–3Galβ1–4]$_n$GlcNAcβ1–4GlcNAc—, where n is a number from the series from 1 to 8;
SAα2–3Galβ1–3[GlcNAcβ1–3Galβ1–4]$_n$GlcNAcβ1–4GlcNAc—, where n is a number from the series from 1 to 8;
Galβ1–4(Fucα1–3)GlcNAcβ1–3[Galβ1–4(Fucα1–3)$_m$GlcNAcβ 1–3]$_n$—Galβ1–4GlcNAcβ1–4GlcNAc—, where m is a number from the series from 0 to 1 and where n is a number from the series from 1 to 4;
Galβ1–3(Fucα1–4)GlcNAcβ1–3[Galβ1–4(Fucα1–3)$_m$GlcNAcβ 1–3]$_n$—Galβ1–4GlcNAcβ1–4GlcNAc—, where m is a number from the series from 0 to 1 and where n is a number from the series from 1 to 4;
SAα2–3Galβ1–3(Fucα1–4)GlcNAcβ1–3[Galβ1–4GlcNAcβ1–3]$_n$—Galβ1–4GlcNAcβ1–4GlcNAc—, where n is a number from the series from 1 to 6;
(GlcNAcβ1–3Galβ1–4)$_n$GlcNAcβ1–3Gal, where n is a number from the series from 1 to 8;
SAα2–6Gal—;
SAα2–6Galβ1–4(GlcNAcβ1–3Galβ1–4)$_n$GlcNAcβ1–3Gal, where n is a number from the series from 1 to 10;
SAα2–3Gal—; and
SAα2–3Galβ1–4(GlcNAcβ1–3Galβ1–4)$_n$GlcNAcβ1–3Gal—, where n is a number from the series from 1 to 10.

Examples of preferred embodiments of the carbohydrate portion are sialyl-Lewis X, sialyl-Lewis A, VIM-2 and the following blood-group determinants Lewis A, B, X, Y and A type¹, A type², B type¹, B type² and H type¹, H type². R. U. Lemieux, *Chem. Soc. Rev.* 7:423 (1978) and 18:347 (1989).

Examples of most preferred embodiments of the carbohydrate portion are sialyl-Lewis X, sialyl-Lewis A or VIM-2. The formula of sialyl-Lewis X is NeuNAcα2–3Galβ1–4(Fucα1–3)GlcNAc and of sialyl-Lewis A NeuNAcα2–3-Galβ1–3(Fucα1–4) GlcNAc. The formula of VIM-2 is NeuNAcα2–3Galβ1–4GlcNAcβ1–3Galβ1–4(Fucα1–3)GlcNAc.

The carbohydrate-containing polymer is synthesized on the laboratory scale, meaning that the molecule is synthesized in milligram-to-gram quantity while intermediates required for its synthesis, i.e., the hydrophilic biodegradable polymer, the bifunctional spacer and the potentiator, can be prepared in gram to kilogram quantity. The carbohydrate portion of the blocker, however, is an exception as it can be synthesized only in quantities ranging milligrams up to one gram. The known synthetic strategies for preparation of oligosaccharides, useful for generating the carbohydrate portion of these molecules, employ purification by column chromatography on silica gel for reactions that do not normally provide a quantitative yield. This purification process is generally too costly and elaborate for industrial needs and is, at the most, employed for purifying final products or valuable intermediates.

In addition, heavy metal compounds are very often used in the synthesis of oligosaccharides according to present invention. There are great objections to their use in the synthesis of substances intended as pharmaceuticals. Thus, with a view towards authorization of the claimed carbohydrate-containing polymers for use as human pharmaceuticals, optional strategies for synthesis without heavy metals are preferred.

SPACER

The spacer is a moiety which connects, and provides spatial separation to the carbohydrate portion and the hydrophilic polymer portion. This spatial separation is necessary to prevent steric interactions between carbohydrate portion and the polymer, thereby ensuring optimal steric accessibility of the carbohydrate portion. The spacer can be a naturally occurring molecule or a non-naturally occurring synthetic molecule.

The facilitate coupling of the spacer to the carbohydrate and polymer portions, the spacer advantageously is bifunctional. A bifunctional spacer is a spacer which carries two reactive functional units which may be used to link the spacer to the polymer portion on the one hand, and to the carbohydrate portion on the other hand, by formation of covalent bonds.

One example of a spacer useful in the compounds of this invention is $-A_1-[B-C_x]_y-D_z-A_2-$, wherein x is 0 or 1;

y is 1, 2, 3, 4, 5, 6 or 7;

z is 0 or 1, with the proviso that z can be 1 only when x is 1;

B and D can be identical or different and are alkylene with 0 to 30 carbon atoms, preferably 0 to 15 carbon atoms, and particularly preferably 0 to 10 carbon atoms, which can be straight-chain, branched or cyclic, are unsubstituted or substituted and can contain single and/or double bonds or 1 to 3 aromatic rings;

C is a substituent of the following formula:

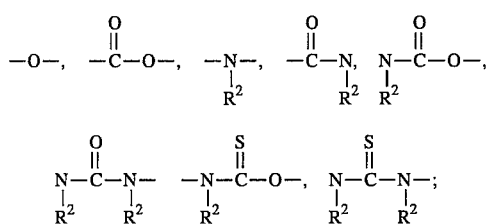

the repetitive units defined by the substituents y can be identical or different; and $A_1$ and $A_2$ are identical or different and are produced by covalent linkage of a reactive group with an activated group $A_1$ and $A_2$ can be identical or different.

$A_1/A_2$ arises from the covalent linkage of, in each case, one reactive to one activated group.

B and D, independent of one another, preferably contain the following substituents: hydroxyl, alkoxy, carboxyl, amino and carboxyalkyl groups of the formula $CO_2-R^1$ where $R^1$ is H or $C_1-C_6$alkyl, preferably $R^1$ is H or $C_1-C_4$-alkyl, and particularly preferably $R^1$ is H or $C_1-C_2$-alkyl.

For C, the following are preferred:

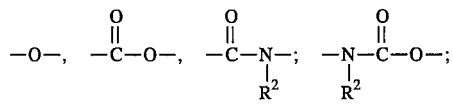

where $R^2$ can be, independent of one another, hydrogen, methyl, ethyl, benzyl, propyl, acetyl or benzoyl.

"Reactive groups" are functional groups which act as donor, preferably OH, $NH_2$ of SH functionalities, which react with "activated groups" to form a covalent bond. Particularly preferred in this regard are $NH_2$ or the OH group. Reactive groups actually are components of the polymer, as the polymer is composed of monomers which contain reactive groups.

"Activated groups" are functional groups which act as acceptor and react with the "reactive groups" to form a covalent bond. Preferably used are bromides, iodides, active esters, particularly preferably p-nitrophenyl or N-hydroxysuccinimide derivatives. Also preferred are carbonyl chlorides and imidazolides of carboxylic acids, mixed carboxylic anhydrides, particularly preferably composed of the following units:

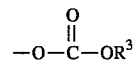

where $R^3$ is $C_1-C_6$, straight-chain or branched, as well as phenyl radicals. Preferably used are aldehydes, acrylic esters, acrylamides, malonimide, succinimide, 2-vinylpyridine, iodoacetic esters, isothiocyanate and/or isocyanate. Most preferred are N-hydroxysuccinimide active radicals, maleimide, succinimide, acrylamides, aldehyde or isocyanate. Activated groups are either present as part of the polymer or can be prepared from reactive groups which are already part of the polymer by processes known to the skilled worker. R. C. Larock, *COMPREHENSIVE ORGANIC TRANSFORMATIONS*, VCK-Verlagsgesellschaft, Weinheim/Germany (1989).

Where such spacers are used, the compounds of this invention have the following general formula: (carbohydrate)—$A_1$—[B—$C_x$]$_y$—$D_z$—$A_2$-(polymer-potentiator). As discussed below, such bifunctional spacers also may be used to link the polymer portion to the potentiator moiety.

POTENTIATOR

The role of the potentiator is to improve the overall reactivity of the compounds of this invention. Thus, the potentiator can improve the reactivity and, hence, affinity of the receptor binding portion of the molecule. Advantageously, the potentiator moiety is a crosslinking moiety located within the hydrophilic polymer or a hydrophobic, hydrophilic or ionic moiety.

One way in which potentiators can work is to influence the conformation of the polymer to achieve improved presentation and, thus, an improved accessibility of the carbohydrate group (or ligand) to a reactive site such as a receptor. In addition, the potentiator can improve solubility of certain soluble-deficient carbohydrate-containing polymers, thereby improving the overall reactivity of the compound in aqueous solutions. Finally, the potentiator may improve the electrostatic interaction of a blocker with its cognate receptor.

An intramolecular crosslinking moiety can carry two reactive, functional units which are used for the covalent linkage to two reactive, functional units which are part of the polymer. One such intramolecular crosslinking moiety can have the formula:

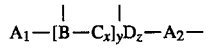

where x is 0 or 1;

y is 1, 2;

z is 0 or 1 with the proviso that z can only be 1 when x is 1;

B or D are identical or different and are alkylene with 0–20 carbon atoms, preferably 0–15 carbon atoms and particularly preferably 0–10 carbon atoms, which can be straight-chain or branched or cyclic, are unsubstituted or substituted and can contain single and/or double bonds or 1–2 aromatic rings.

C is a substituent of the following formula:

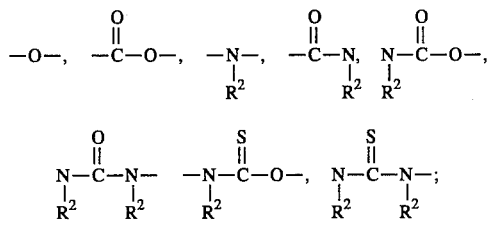

where $R^2$ can, independently of one another, be hydrogen, methyl, ethyl, benzyl, propyl, acetyl or benzoyl;

$A_1$ and $A_2$ have the meanings already mentioned for the spacer; and the repetitive units defined by the substituent y can be identical or different.

Preferred substituents for B or D are additionally hydroxyl, alkoxy, amino, carboxyl and carboxyalkyl groups of the formula $CO_2R^4$ where $R^4$ is H or $C_1$–$C_6$, particularly preferably $C_1$–$C_4$, and very particularly preferably $C_1$–$C_2$ or preferably carbonylamino and carbonylaminoalkyl groups of the formula $CONR^5R^6$ where $R^5$ and $R^6$ can be identical or different and are H or $C_1$–$C_4$-alkyl; R is particularly preferably H or $C_1$–$C_2$-alkyl.

Preferred forms of C are

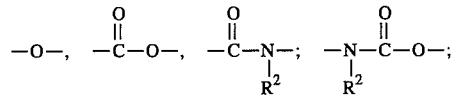

Hydrophobic, hydrophilic and ionic or ionizable groups are substituents which carry a reactive functional unit and can react with another reactive functional unit on the polymer moiety to form a covalent bond. The number of groups employed depends on the extent to which the conformation of the polymer is to be influenced.

Hydrophobic substituents are molecules which have a hydrophobic surface and which carry a reactive functional unit such as, for example, alcohols, amines, active esters or acid chlorides of cyclododecane, adamantane, 2-methylpropane, 2,2-dimethylpropane and the fullerenes.

Hydrophilic substituents are molecules which have a hydrophilic surface and which carry a reactive functional unit such as, for example, substituted or unsubstituted cyclodextrins, mono- and oligosaccharides.

Ionic or ionizable substituents are molecules which contain polar, ionic or ionizable groups and carry a reactive functional unit such as, for example, purines, pyridines, lysine and compounds with a plurality of carboxylic, phosphonic or sulfonic acid groups on a short alkyl chain ($C_1$–$C_8$) which can be branched, unbranched or cyclic and contains a reactive group, such as, for example, tartaric acid and aspartic acid. Also included are polar compounds which are readily soluble in water, such as polyols, polyethylene glycols, amino alcohols or compounds with a plurality of carboxylic, phosphonic or sulfonic acid groups on a short alkyl chain, preferably $C_1$–$C_8$, which can be branched, unbranched or cyclic.

ADDITIONAL MOLECULAR COMPONENTS

In addition to the above-mentioned compounds, it is possible to couple substituents to the compound such as a marker group or label, and/or a drug or other active agent. Generally, the marker group or label makes it possible to use the carbohydrate-containing polymer for in vitro or in vivo diagnoses. The coupling of the marker to the polymer generally takes place via covalent bonds. Markers known to the skilled artisan for use in in vivo diagnosis may be employed for this purpose, such as, for example, radioactive markers which contain a bound radionuclide (e.g., technetium), X-ray contrast agents (e.g., iodinated compounds), as well as magnetic resonance contrast agents (e.g., gadolinium compounds). The relative proportion of marker to the entire molecule generally less than about 1% in terms of molecular weight.

In selecting a drug for coupling to the polymer moiety, the drug would be chosen in reference to the particular disorder to be treated and the regimen involved. The coupling of the drug to the polymer generally occurs through covalent or ionic bonds. Exemplary drugs which could be bound to the carbohydrate-containing polymers of this invention include:

antitumor agents such as, for example, daunomycin, doxorubicin, vinblastine, bleomycin;

antibiotics such as, for example, penicillins, erythromycins, azidamfenicol, cefalotin and griseofulvin;

immunomodulators such as, for example, FK-506, azathioprine, levamisole;

antagonists of blood platelet activation factors;

leukotriene antagonists;

inhibitors of the cyclooxygenase system such as, for example, salicylic acid compounds;

lipoxygenase inhibitors, antiinflammatory agents such as, for example, indomethacin;

antirheumatic agents such as, for example, nifenazone.

Advantageously, the carbohydrate-containing polymers of this invention are able to react with all naturally occurring receptors which specifically recognize in vivo the carbohydrate portion of ligands. These preferably are receptors which are expressed on cell surfaces, for example, by mammalian cells including human cells, bacterial cells or viruses. Also preferred are hormones and toxins, and recognizing receptors which recognize hormones or toxins. Particularly preferred cell surface receptors are those which belong to the class of selectins. Most particularly preferred receptors are those expressed in inflammatory disorders, for example Leu-8 (=L-selectin=gp90$^{mel}$=LAM-1= LEC-CAM-1), ELAM-1 (=E-selectin) and GMP-140 (=P-selectin= CD62=PADGEM).

If the carbohydrate-containing polymers of this invention are employed as antiadhesion therapeutic agents, the aim is that, in the case of inflammations, they prevent the ELAM-1 receptors on stimulated endothelial cells binding to sialyl-Lewis X structures on the surface of leukocytes. In the case of influenza therapy, the carbohydrate-containing molecules prevent the adhesion of viruses to the neuraminic acid on the cell surface and thus also the endocytosis of the virus particles.

PREPARATION OF THE CARBOHYDRATE-CONTAINING POLYMER ACCORDING TO THE INVENTION

As discussed above, the carbohydrate-containing polymer according to the invention is composed of a carbohydrate portion, spacer portion, hydrophilic polymer portion and a potentiator moiety. Generally, the molecule is synthesized by forming a covalent bond between the carbohydrate portion and the bifunctional spacer, followed by subsequent covalent linkage of the carbohydrate portion-spacer complex to the polymer and finally, covalent linkage to the potentiator.

The linkage can alternatively take place in other sequences:

Reactions of the polymer with the potentiator on the one hand and, of the carbohydrate portion with the bifunctional spacer on the other hand, to form covalent bonds. Covalent linkage of the polymer-potentiator complex to the carbohydrate portion-spacer complete the synthesis.

Covalent linkage of the polymer and potentiator results in a compound which can then reacted with the spacer to form a covalent bond. Covalent reaction of this compound with the carbohydrate portion results in formation of the carbohydrate-containing polymer according to the invention.

The carbohydrate-containing molecule can be synthesized by covalent linkage of the polymer to the bifunctional spacer, covalent linkage of this first product to the carbohydrate portion and subsequently reaction of this second product with the potentiator.

The polymer may be linked to the spacer in a first reaction step, followed by covalent linkage to the potentiator and then to the carbohydrate portion, whereby the synthesis is completed.

The first-mentioned synthetic route and the first-mentioned alternative synthetic route are preferred.

The synthesis of the carbohydrate-containing polymer by covalent linkage of its components takes place by reaction of reactive with activated groups. The distribution of reactive and activated groups on the four components is in this case of no importance to the general practicability of the synthesis.

The reaction between reactive and activated groups takes place by processes known to the skilled worker, by esterification, amidation, addition to a double bond and alkylation. R. C. Larock, *COMPREHENSIVE ORGANIC TRANSFORMATION*, VCH-Verlagsgesellschaft, Weinheim, Germany, (1989); Tietze and Eichler, *REAKTIONEN UND SYNTHESEN IM ORG.-CHEM. PRAKTIKUM* (Reactions and Syntheses in Practical Org. Chem.), G. Thieme Verlag, Stuttgart, Germany (1981).

THE CARBOHYDRATE PORTION AND ITS LINKAGE TO THE SPACER

The carbohydrate portion can originate from natural sources or be prepared chemically, chemoenzymatically or enzymatically. Suitable natural sources for carbohydrates are known to the skilled artisan and are referenced in the appropriate literature. See, for example, *Biochemistry, Biol. Chem. Hoppe-Seyl. J. Biol. Chem., Biochemistry and Cell Biology, Cell*. Established processes, known to the skilled artisan, for the purification of oligosaccharides are likewise described therein. Carbohydrates originating from naturally sources are always found in the form of a "free reducing end."

Processes for the chemical, enzymatic or chemoenzymatic synthesis of carbohydrates which are recognized by cell surface receptors are known to the skilled worker from the chemical literature and from review articles. For the chemical synthesis for example *CARBOHYDRATE RESEARCH*, Elsevier Science Publishers B.U., Amsterdam, Journal of Carbohydrate Chemistry, Marcel Dekker, Inc., New York; H. Paulsen, *Angewandte Chemie* 94:184 (1982); R. R. Schmidt, *Angewandte Chemie*, 98:213 (1987); H. Kunz, *Angewandte Chemie* 44:247 (1987); H. Paulsen, *Angewandte Chemie* 102:851 (1990). For the enzymatic synthesis for example *CARBOHYDRATE RESEARCH*, Elsevier Science Publishers B. U., Amsterdam; *Journal of Carbohydrate Chemistry*, Marcel Dekker, Inc., New York, David et al., *Advances in Carbohydrate Chemistry and Biochemistry* 49:1975 (1991); Nielsson, *Applied Biocatalysis* 1:117 (1991); Drueckhammer et al., *Synthesis* 499 (1991). Chemoenzymatic synthesis is defined as the combination of chemical and enzymatic reaction steps for the synthesis of the carbohydrate portion and of a covalent linkage of carbohydrate portion and spacer.

Synthetically prepared oligosaccharides can be obtained both with a free reducing end and in a spacer-linked form. The introduction of the spacer takes place by processes known to the skilled artisan for chemical or enzymatic glycosylation (see above). The preferred preparation processes are those which result in an oligosaccharide already covalently linked to the spacer.

The coupling of the carbohydrate portion with a free reducing end to the spacer takes place via a covalent bond. The following processes can be carried out for the coupling:

The oligosaccharide with free reducing end is converted, for example, by analogy to the process of Lundquist et al., *J. Carbohydrate Chem.* 10:377 (1991), into the free 1-aminoglycoside which is subsequently covalently linked to a spacer by acylation. Alternatively, the compound may be covalently linked, for example, by analogy to the process of Kochetkow, *Carbohydrate Research* 146:C1 (1986), to the spacer using an N-hydroxysuccinimide active ester as activated group on the spacer.

The free reducing end of the oligosaccharide can be converted to a lactone, by analogy, to the process of Isebell et al., in METHODS OF CARBOHYDRATE CHEMISTRY, Academic Press, New York (1962), using iodine and potassium hydroxide. This lactone can be covalently linked to the spacer, for example, by means of a primary amino group which is a component of the latter. Id.

The formation of a covalent bond between the reducing end of an oligosaccharide and the spacer also is possible by reductive amination. This method employs a spacer having a primary amino group at the appropriate end, for example, by analogy to Lane, *Synthesis* 135 (1975).

If the oligosaccharide contains, at its reducing end, an amino sugar with a free amino group, the latter can be covalently linked to the spacer, for example, by analogy to the process of Kochetkow, *Carbohydrate Research* 146:C1 (1986), by means of an N-hydroxysuccinimide active ester of the latter.

LINKAGE OF THE SPACER TO THE POLYMER

The covalent linkage of the polymer (i) to the spacer or (ii) to a compound composed of covalently linked spacer and carbohydrate and of a covalent compound of polymer and potentiator with the spacer or (iii) to a compound composed of covalently linked spacer and carbohydrate, takes place by reaction between a reactive group and an activated group. In this link, it is possible for (a) the reactive group to be located at the end of the spacer or at the end of a compound composed of a covalently linked spacer and carbohydrate moiety and the activated group to be located on the polymer or on a compound composed of a covalently linked polymer and potentiator and (b) for the activated group to be located at the end of the spacer or at the end of a compound composed of a covalently linked spacer and carbohydrate moiety and the reactive group to be located on the polymer or on a compound composed of covalently linked polymer and a potentiator.

The reaction between a reactive group and an activated group takes place by processes known to the skilled artisan, for example, esterification, amidation, addition to a double bond and alkylation. See, for example, R. C. Larock, *COMPREHENSIVE ORGANIC TRANSFORMATIONS*, VCH Verlagsgesellschaft Weinheim, Germany (1989); Tietze and Eicher, *REAKTIONEN UND SYNTHESEN IM ORG.- CHEM. PRAKTIKUM* (Reactions and Syntheses in Practical Org. Chem.), G. Thieme Verlag, Stuttgart, Germany (1981).

PREPARATION OF A HYDROPHILIC POLYMER

The preparation of a hydrophilic polymer takes place by processes known to the skilled artisan. See, for example, in H. G. Elias, *MAKROMOLEKÜLE* (Macromolecules), Vols. 1 and 2, Hüthig & Wepf Verlag, Basle, Switzerland (1991/92) and D. Braun et al., *PRAKTIKUM DER MAKROMOLEKULAREN, ORGANISCHEN CHEMIE* (Practical Macromolecular Organic Chemistry), Hüthig-Verlag (1979).

ATTACHMENT OF THE POTENTIATOR

As discussed above, the potentiator is covalently linked to the polymer portion of the carbohydrate-containing polymer. Advantageously, the covalent linkage between potentiator and polymer can be achieved by reaction of a reactive group with an activated group. The reaction between reactive groups and activated groups takes place by processes known to the skilled artisan, for example, alkylation, acrylation or addition to a double bond. See, for example, R. C. Larock, *COMPREHENSIVE ORGANIC TRANSFORMATIONS*, VCH Verlagsgesellschaft Weinheim, Germany (1989) and Tietze and Eicher, *REAKTIONEN UND SYNTHESEN IM ORG. CHEM. PRAKTIKUM* (Reactions and Syntheses in Practical Org. Chem.), G. Thieme Verlag, Stuttgart, Germany (1981).

The preparation of the carbohydrate-containing polymer, as an alternative to the chemical synthetic routes mentioned above, can take place via an enzymatic or chemoenzymatic linkage of the individual components. The enzymes used in such processes are glycosidases, glycosyltransferases, transglycosidases and/or lipases. Glycosidases, glycosyltransferases and/or transglycosidases preferably are employed to construct the carbohydrate portion and to link carbohydrate portion and spacer. Lipases such as, for example, from *Pseudomonas, Candida,* Mucor or Rhizopus preferably are used for linking the reactive group to the activated group. Activated groups employed in this case are carboxylic acids, methyl esters and/or vinyl esters.

The processes described above are merely some embodiments of the present invention and are mentioned by way of example. It will be apparent to the skilled artisan that other processes and reagents are suitable and within the spirit of the present invention. Thus, the foregoing general processes should be read as limiting the scope of the present invention.

DIAGNOSTIC AND THERAPEUTIC USE OF THE CARBOHYDRATE-CONTAINING POLYMER ACCORDING TO THE PRESENT INVENTION

Some embodiments of the carbohydrate-containing polymers according to the present invention may be useful both as reagents for in vitro, in situ and in vivo diagnosis of disease as well as in vivo therapy. For example, cells from diseased patients may be treated with a battery of compounds to diagnose the particular receptor aberration causing the disease state. WO 92/02527 provides an example of such a diagnostic use. By the same token, this sort of diagnostic scheme could be used in situ or in vivo with the compounds of the present invention because of their non-toxicity, clearance from the body and relatively high affinity.

The same features that facilitate in vivo diagnosis also permit the use of molecules according to the present invention as therapeutic agents. A variety of different infectious and inflammatory diseases are dependent, at one level or another, on the expression of pathogenic receptors. In the case of infectious disorders, the receptor may be a receptor for an infectious agent. In the case of inflammatory disorders, the receptor may be specific for a ligand on the surface of an immune response cell, the binding which sequesters and/or activates the immune response cell.

As mentioned previously, where in vivo use is desired, the carbohydrate-containing polymers should not display any adverse side effects upon administration. For example, in the case of intravenous use, hemolytic and immunogenic properties should be avoided. Enzymes in the blood coagulation cascade should not be activated in order to avoid thrombus formation. In addition, unused molecules should be metabolized to non-toxic substances or be excreted.

Additionally, for optimal therapeutic and/or diagnostic use of these carbohydrate-containing polymers, the degree of loading of the polymer with the oligosaccharide should be within a defined range of from about 0.5 to about 50%, preferably from about 2 to about 20%. Also, the length of the spacer which links the polymer to the carbohydrate is preferably in the range of 3–30 atoms. Finally, the half-life of the molecule is controlled by the nature and degradability of the polymer portion and the overall molecular weight of the blocker. The circulatory lifetime of the molecule can be adjusted from one minute to several hours to several days.

The carbohydrate-containing polymers according to the invention, and their physiologically tolerated salts, are intended for use as medicines in mammals, especially humans. The pharmaceuticals are preferably suited for the prophylaxis and/or therapy of bacterial and viral infections and of diseases which involve inflammatory processes. This latter group includes post-infarct syndrome, shock lung in adults, shock, stroke, acute and chronic organic rejection, vasculitis, sepsis, inflammatory disorders of the skin, rheumatoid arthritis and metastic tumors.

PHARMACEUTICALS

The pharmaceutical products are preferably produced and administered in dosage units. Preferred in the case of solid dosage units are tablets, capsules and suppositories. The pharmaceuticals according to the invention are produced by converting the carbohydrate-containing polymer with conventional excipients and, where appropriate, additives and/or ancillary substances into the or a suitable dosage form.

Examples of suitable solid or liquid pharmaceutical presentations are granules, powders, tablets, coated tablets, (micro)capsules, suppositories, syrups, emulsions, suspensions, aerosols, drops or injectable solutions in ampoule form as well as products with protracted release of active substance, in the production of which it is customary to use excipients and additives and/or aids such as disintegrants, binders, coating agents, swelling agents, glidants or lubricants, flavorings, thickeners or solubilizers. Examples of commonly used excipients or ancillary substances which may be included are magnesium carbonate, titanium dioxide, lactose, mannitol and other sugars, talc, lactalbumin, gelatin, starch, vitamins, cellulose and its derivatives, animal and vegetable oils, polyethylene glycols and solvents such as, for example, sterile water, alcohols, glycerol and polyhydric alcohols.

The pharmaceuticals according to the invention are generally administered intravenously, orally or parenterally or as implants, but rectal use is also feasible. The daily doses necessary for the treatment of a patient vary depending on the activity of the molecule, the mode of administration, the nature and severity of the disorder and the age and body weight of the patient, etc. The daily dose can be administered either by a single administration, in the form of a single dosage unit, or as a plurality of small dosage units or by multiple administration of divided doses at particular intervals, the daily dose change during the course of treatment depending on the number of receptors expressed during a particular phase of the disease. It is conceivable that only a few receptors are expressed on the cell surface in the initial stage of a disease and, accordingly, the daily dose to be administered would be less than that for patients suffering a well-progressed disease.

EXAMPLES

A. ASSAY FOR INVESTIGATING THE EFFECT OF CARBOHYDRATE-CONTAINING POLYMERS ON CELL ADHESION, FACILITATED BY RECOMBINANT SOLUBLE SELECTIN AND CD4 FUSION PROTEINS.

This assay is used to detect the effect of polymer-bound carbohydrate units on selectin-driven cell adhesion of promyelocytic cells. The assay used to test the activity of these molecules on the interaction between E- and P-selectins (old nomenclature ELAM-1 and GMP-140 respectively) and their ligands is specific for only one of these interactions in each case. The ligands are offered in their natural form as surface structures on promyelocytic HL60 cells. Since HL60 cells have ligands and adhesion molecules which differ widely in specificity, the required specificity of the assay can be provided only via the binding partner. Used as binding partners were genetically engineered soluble fusion proteins from the extracytoplasmis domain in each case of E- and P-selectin and the constant region of a human immunoglobulin of subclass IgG1.

A1. Preparation of L-selectin-IgG1.

The genetic construct "ELAM-Rg," published by Walz et al., *Science* 250:1132–1135 (1990), was used to prepare soluble L-selectin-IgG1 fusion protein. For expression of recombinant selectin, plasmid DNA was transfected into COS-7 cells (ATCC) using DEAE-dextran. See Ausubel, F. M., Brent, R., Kingston, R. E., Moore, D. D., Seidman, J. G., Struhl, K. and Smith, J. A. in *CURRENT PROTOCOLS IN MOLECULAR BIOLOGY*, John Wiley, New York (1991). Seven days after transfection, culture supernatant is obtained, centrifuged to remove cells and cell fragments and adjusted to 25 mM Hepes (pH 7.0), 0.3 mM PMSF, 0.02% sodium axide and stored at +4° C.

A2. Preparation of P-selectin-IgG1.

The genetic construct "CD62Rg" published by Aruffo et al., *Cell* 67:35–44 (1991), is used to prepare the soluble P-selectin-IgG1 fusion protein. The subsequent procedure corresponds to the preparation of L-selectin-IgG1 described under A1.

A3. Preparation of CD4-IgG1.

The genetic construct "CD4:IgG1 hinge" published by Zettlemeissl et al., *DNA and Cell Biology* 9:347–353 (1990), is used to prepare the soluble CD4-IgG1 fusion protein. The subsequent procedure corresponds to the preparation of L-selectin-IgG1 described under A1.

A4. Procedure for the HL60 cell adhesion assay for recombinant soluble adhesion molecules.

96-well microtiter assay plates (Nunc Maxisorb) are mixed with 100 μl of a goat anti-human IgG antibody (Sigma) diluted (1/100) in 50 mM Tris pH 9.5 and incubated at room temperature for 2 hours. Removal of the antibody solution is followed by one wash with PBS.

One hundred and fifty µl of blocking buffer is left in each well at room temperature for 1 h (blocking buffer=0.1% gelatin, 1% BSA, 5% calf serum, 0.2 mM PMSF, 0.02% sodium azide). Removal of the blocking buffer is followed by one wash with PBS.

One hundred µl of cell culture supernatant from appropriately transfected and recombinant-expressing COS cells are pipetted into each of the wells and incubate at room temperature for 2 hours. Removal of the cell culture supernatant is followed by one wash with PBS.

Twenty µl of binding buffer is placed in the wells (binding buffer=50 mM Hepes, pH 7.5; 100 mM NaCl; 1 mg/ml BSA; 2 mM $MgCl_2$; 1 mM $CaCl_2$; 3 mM $MnCl_2$; 0.02% sodium azide; 0.2 mM PMSF). Five µl of the test substance is added by pipette, mixed by agitating the plate and incubated at room temperature for 10 min.

Fifty ml of an HL60 cell culture with 200,000 cells/ml is centrifuged at 350 g for 4 min. The pellet is resuspended in 10 ml of RPMI 1640 and the cells are again centrifuged. For labeling of the cells, 50 µg of BCECF-AM (molecular probes) are dissolved in 5 µl of anhydrous DMSO and, subsequently, 1.5 ml of RPMI 1640 are added to the BCECF-AM/DMSO solution. The cells are resuspended in this solution and incubated at 37° C. for 30 min. After centrifugation at 350 g for 2 min., the labeled cell pellet is resuspended in 11 ml of binding buffer, and the resuspended cells are distributed in 100 µl aliquots in the wells of the microtiter plate. The plate is left to stand at room temperature for 10 min in order to allow the cells to sediment to the bottom of the test plate. This also permit the cells to adhere to the coated wells.

To stop the assay, the microtiter plate is completely immersed at an angle of 45° in stop buffer (stop buffer=25 mM Tris, pH 7.5; 125 mM NaCl; 0.1% BSA; 2 mM $MgCl_2$; 1 mM $CaCl_2$; 3 mM $MnCl_2$; 0.02% sodium azide). The stop buffer is removed from the wells by inversion, and the procedure is repeated two more times.

The BCECF-AM-labeled cells which are firmly adherent in the wells are measured in a cytofluorimeter (Millipore) with a sensitivity setting of 4, an excitation wavelength of 485/22 nm and an emission wavelength of 530/25 nm.

B. ASSAY TO INVESTIGATE THE EFFECT OF CARBOHYDRATE-CONTAINING POLYMERS ON CELL ADHESION, FACILITATED BY STIMULATION OF HUMAN ENDOTHELIAL CELLS.

Testing of the activity of carbohydrate-containing polymers on cell adhesion to recombinant soluble fusion proteins is a highly specific assay which is based on the interaction of only one type of adhesion molecule with its corresponding ligand. In order to simulate more complex in vivo cell-cell interactions, we use an assay in which HL60 cells adhere to stimulated human umbilical endothelial cells.

B1. Obtaining human umbilical endothelial cells (HUVEC).

Umbilical cords are stored after delivery in PBS containing 100,000 IU/L penicillin, 100 mg/L streptomycin, 50 mg/L gentamicin, 50,000 IU/L mycostatin at =4° C. until further processed.

The longest undamaged pieces are cut out of the umbilical cord with a scalpel and placed on fresh aluminum foil. One end of the umbilical cord is closed with a clip. At the other end, a suitable tube is inserted into the umbilical vein and fixed by ligating the end of the umbilical cord. The vein is filled through the inserted tube with collagenase solution (50 mg collagenase/100 ml 25 mM Hepes, pH 7.0) and incubated at 37° C. for 15 min. In order to increase the cell yield, the umbilical cord is gently massaged after the incubation in order to detach still adherent endothelial cells. The cell suspension is subsequently allowed to run out of the vein into a culture tube containing cell culture medium and 10% fetal calf serum. The vein is then washed with PBS in order to obtain the remaining cells.

The cell suspension is centrifuged at 500 g for 5 min. The cell pellet subsequently is resuspended in 4 ml of culture medium and the cells are plated out. After 3–4 days, confluent growth of the cells should be seen. Once confluent growth is achieved, the cells may be passaged. To check the purity of the endothelial cell culture, the culture is stained with a fluorescently-tagged antibody against factor VIII. A positive reaction is shown only by endothelial cells but not by potentially contaminating fibroblasts.

B2. Procedure for the assay.

Twenty thousand endothelial cells are plated per well in a 96-well microtiter plate and incubated at 37° C. for 24 hours (for this assay, the endothelial cells must not have been passaged more than 5–6 times). Four hours before the assay the endothelial cells are stimulated by addition of IL-1 (final concentration of 15 U/ml). After removal of the culture medium, the cells are washed once with RPMI medium without serum. Cells are resuspended in 20 µl of RPMI medium followed by addition of test substances.

B3. The further steps in the assay.

Labelling of the HL60 cells and introduction of the HL60 cells are carried out as described in A4, above.

ASSAY TO INVESTIGATE THE EFFECT OF CARBOHYDRATE-CONTAINING POLYMERS ON CELL ADHESION TO FROZEN SECTIONS OF LYMPHATIC TISSUE.

A type of cell-cell interaction that can be examined in situ is that between leukocytes and endothelial cells. The assay employs frozen sections of lymphatic tissue and measures the extent of binding between adhesion molecules on the surface of the endothelial cells in the frozen section and the corresponding ligands on the surface of leukocytes. The assay may be modified by using a variety of differing cells whose surface ligands are well descried in the scientific literature. Adhesion is determined by the number HL60 cells bound to lymph node frozen sections.

Axillary, cervical or mesenteric lymph nodes are dissected out of freshly sacrificed rats and rapidly frozen in liquid nitrogen. Ten µm-thick cryostat sections are prepared from the frozen lymph nodes, transferred to circular cover glasses (diameter 18 mm) and dried at room temperature for 2 h.

Twenty µl of binding buffer is then pipetted onto the sections. The test substances are added and incubated at room temperature for 10 min. HL60 cells are labeled as described above in part A4. Two hundred thousand labeled HL60 cells in 100 µl of binding buffer are added to each cover glass and left to stand for 10 min. This allows the sedimented cells to time reach endothelial cells, to which some of them will adhere. The cover glasses are immersed at an angle of 45° in stop buffer in order to rinse off the non-adherent cells. The cover glasses are subsequently fixed in 4% formaldehyde in PBS at room temperature for 10 min.

Cross sections of lymphatic blood vessels are recorded by photography under an immunofluorescence microscope (FITC excitation). The adherent HL60 cells are clearly distinct from the unstained background. The result is expressed as bound HL60 cells per unit area of endothelium.

D. ASSAY TO INVESTIGATE THE EFFECT OF CARBOHYDRATE-CONTAINING POLYMERS ON LEUKOCYTE ADHESION IN RATS IN VIVO.

It is known that some circulating white blood cells tend to adhere to the intima of the blood vessels and this tendency is considerably enhanced in inflammatory processes. Leukocytes normally impinge continually on the blood vessel walls, but this collision is elastic so that the cells rebound to a certain extent and return to the circulation. In inflammatory processes, biochemical changes, both in the leukocytes and in the endothelial cells lining the blood vessels, lead to changes in the surface properties of both types of cell. In essence, the cells' behavior becomes more adhesive. This adhesiveness is initially expressed by the tendency of the leukocytes after collision with the endothelium to roll on the endothelial cells. This rolling of the leukocytes on the endothelium induces further biochemical reactions on both binding partners, as a consequence of which cell adhesion is enhanced. This further enhancement of the adhesiveness slows down the rolling of the leukocytes until they adhere firmly to the endothelium. The firm adherence is followed by the migration of the leukocytes out of the blood vessel.

Microscopic recording of the processes described above is possible on dissected mesenteric tissue, for example from rats. Substances injected into the bloodstream can therefore be investigated to find whether they are able to influence induced leukocyte adhesion. In this way, it has been determined that the rolling of the leukocytes, the firm adhesion and the migration out of the blood vessels can be induced with leukocyte-stimulating factors such as FMLP (f-Met-Leu-Phe), LPS (lipopolysaccharides) or TNF (tumor necrosis factor). The method described below is used to establish the in vivo activity of substances which inhibit these adhesive actions of leukocytes and the vessel intima.

Rats are anesthetized for carrying out this investigation. The abdominal cavity is opened and a section of the small intestine is pulled out. The section of small intestine is continuously kept moist on a heatable microscope stage. For microscopic inspection, a region of mesenteric tissue is covered with liquid paraffin. For the control, all the adherent, non-stimulated-leukocytes in this region are counted every 5 min. for a period of 30 min. In parallel, the blood pressure, body temperature and flow rate of the blood are recorded. The test substance is administered by continuous venous infusion throughout the test. After introduction of leukocyte stimulants, added dropwise to the mesenteric tissue, the adherent leukocytes are counted every 5 min. for a period of 90 min.

The investigation is carried out on test groups composed of three animals. The first animal receives only the vehicle in order to determine the spontaneous adhesion. The second animal receives only the leukocyte stimulation in order to determine the pathogenic control. The third animal receives leukocyte stimulant and test substance. The number of adherent leukocytes in the pathogenic control is set equal to 100%. The percentage change in the leukocyte adhesion upon administration of test substance, as compared to the pathogenic control, indicates the activity of a test substance.

E. CHEMICAL SYNTHESES.

The following synthetic procedures are provided by way of example without limiting the manner of synthesis of carbohydrate-containing polymers.

E1. Monosaccharide (Schemes 1 and 7).

2-Amino-2-deoxyglucose hydrochloride [1] is converted by the procedure of Lemieux et al., ACS Symp. Ser. 39:90 (1976), by reaction with phthalic anhydride and subsequent reaction with acetic anhydride/pyridine into 1,3,4,6-tetraacetyl-2-N-acetyl-2-deoxyglucose [2].

Treatment with tin tetrachloride/thiophenol by the methdo of Nicolaou et al., J. Am. Chem. Soc. 112:3695 (1990), results in the corresponding 1-thiophenyl derivative [3]. The latter is reacted by the procedure of Silwanis et al., J. Carbohydr. Chem. 10:1067 (1991), with 6-azidohexanol. The acetyl and phthaloyl protective groups are cleaved with hydrazine hydrate in analogy to the procedure to Nicolaou et al., J. Am. Chem. Soc. 114:3127 (1992). Before elimination of the benzyl protective groups ($H_2/Pd(OH)_2$, MeOH), the free amino group is selectively acetylated in the presence of the free hydroxyl groups with excess acetic anhydride. The result is [4].

E2. Disaccharide (Schemes 1, 2, 5 and 7).

Synthesis of a protected N-acetylglucosamine unit

2-Amino-2-deoxyglucose hydrochloride [1] is converted by the procedure of Lemieux et al., ACS Symp. Ser. 39:90 (1976), by reaction with phthalic anhydride and subsequent reaction with acetic anhydride/pyridine into 1,3,4,6-tetraacetyl-2-N-acetyl-2-deoxyglucose [2].

Treatment with tin tetrachloride/thiophenol by the method of Nicolaou et al., J. Am. Chem. Soc. 112:3695 (1990), results in the corresponding 1-thiophenyl derivative [3]. After elimination of the acetyl protective groups [5], the benzylidene group and the allyl group (benzaldehyde dimethyl acetal/CSA; allyl bromide/NaH) are introduced. Reduction with $NaCNBH_3$ liberates the 4-OH group [6].

Synthesis of a protected galactose unit

Galactose [7] is converted by the procedure of Nicolaou et al., J. Chem. Soc.: Chem. Comm. 870 (1991), by mixing with acetic anhydride/triethylamine/ DMAP and tin tetrachloride/thiophenol into the thioglycoside [8]. After elimination of the acetyl protective groups, compound [9] is produced by reaction with benzaldehyde dimethyl acetal/CSA. Acetylation (acetic anhydride/triethylamine/DMAP) followed by reduction with $NaCNBH_3$ results in the formation of compound [10]. After renewed acetylation (acetic anhydride/triethylamine/DMAP), the thioglycoside is converted by NBS/HF into the fluoride compound [11].

Synthesis of the protected N-acetyllactosamine disaccharide

The galactosyl fluoride [11] is linked to the N-acetylglucosamine derivative [5] by the procedure of Nicolaou et al., J. Chem. Soc.: Chem. Comm. 870 (1991), in the presence of AgClO$_4$/SnCl$_2$ to give compound [12] which is converted by elimination of the allyl protective group (Ru(PPh$_3$)$_4$/H$_2$; TsOH/MeOH) into compound [13]. The latter is reacted with 6-azidohexanol in analogy to the procedure of silwanis et al., J. Carbohydr. Chem. 10:1067 (1991).

The cleavage of the acetyl and phthaloyl protective groups with hydrazine hydrate takes place in analogy to the procedure of Nicolaou et al., J. Am. Chem. Soc. 114:3127 (1992). Before elimination of the benzyl protective groups (H$_2$/Pd(OH)$_2$, MeOH), the free amino group is selectively acetylated in the presence of the free hydroxyl groups with excess acetic anhydride. The result is compound [14].

E3. Trisaccharide (Schemes 1, 2, 3, 5 and 8).

Synthesis of a protected N-acetyl glucose unit

2-Amino-2-deoxyglucose hydrochloride [1] is converted by the procedure of Lemieux et al., ACS Symp. Ser. 39:90 (1976), by reaction with phthalic anhydride and subsequent reaction with acetic anhydride/pyridine into 1,3,4,6-tetraacetyl-2-N-acetyl-2-deoxyglucose [2].

Treatment with tin tetrachloride/thiophenol by the method of Nicolaou et al., J. Am. Chem. soc. 112:3695 (1990), results in the corresponding 1-thiphenyl derivative [4]. After elimination of the acetyl protective groups [5], the benzylidene group and the allyl group (benzaldehyde dimethyl acetal/CSA; allyl bromide/NaH) are introduced. Reduction with NaCNBH$_3$ results in liberation of the 4-OH group [6].

Synthesis of a protected galactose unit

Galactose [7] is converted by the procedure of Nicolaou et al., J. Chem. Soc.: Chem. Comm. 870 (1991), by mixing with acetic anhydride/triethylamine/DMAP and tin tetrachloride/thiophenol into the thioglycoside [8]. After elimination of the acetyl protective groups, compound [9] is produced by reaction with benzaldehyde dimethyl acetyl/CSA. Acetylation (acetic anhydride/triethylamine/ DMAP) followed by reduction with NaCNBH$_3$ results in compound [10]. After renewed acetylation (acetic anhydride/triethylamine/DMAP), the thioglycoside is converted by NBS/HF into the fluoride compound [11].

Synthesis of a protected focuse unit

Fucose [15] is peracetylated (acetic anhydride/triethylamine/DMAP) by the procedure of Nicolaou et al., J. Am. Chem. Soc. 112:3694 (1990), and converted with tin tetrachloride/thiophenol into the thioglycoside [16]. Subsequently, after a replacement of the acetyl by benzyl protective groups (NaOMe/MeOH; NaH/BnBr), the thiophenol is converted with NBS/HF or NBS/DAST into the fluoride compound [17].

Synthesis of the protected N-acetyllactosamine disaccharide

The galactosyl fluoride [11] is linked to the N-acetylglucosamine derivative [5] by the procedure of Nicolaou et al., J. Chem. Soc.: Chem. Comm. 870 (1991), in the presence of AgClO$_4$/SnCl$_2$ to give compound [12] which is converted by elimination of the allyl protective group (Ru(PPh$_3$)$_4$/H$_2$; TsOH/MeOH) into compound [13].

Synthesis of the protected Lewis X trisaccharide

The disaccharide [13] is reacted with the fucosyl fluoride [17] (AgClO$_4$/SnCl$_2$) by the procedure of Nicolaou et al., J. Chem. soc.: Chem. Comm. 870 (1991), to give the Lewis X derivative [18]. The latter is reacted with analogy to the procedure of Silwanis et al., J. Carbohydr. Chem. 10:1067 (1991), with 6-azidohexanol.

The cleavage of the acetyl and phthaloyl protective groups with hydrazine hydrate takes place in analogy to the procedure of Nicolaou et al., J. Am. Chem. Soc. 114:3127 (1992). Before elimination of the benzyl protective groups (H$_2$/Pd(OH)$_2$, MeOH), the free amino group is selectively acetylated in the presence of the free hydroxyl groups with excess acetic anhydride. The result is compound [19].

E4. Tetrasaccharide (Schemes 1–6 and 8).

Synthesis of a protected N-acetyl glucose unit

2-Amino-2-deoxyglucose hydrochloride [1] is converted by the procedure of Lemieux et al., ACS Symp. Ser. 39:90 (1976), by reaction with phthalic anhydride and subsequent reaction with acetic anhydride/pyridine into 1,3,4,6-tetraacetyl-2-N-acetyl-2-deoxyglucose [2].

Treatment with tin tetrachloride/thiophenol by the method of Nicolaou et al., J. Am. Chem. Soc. 112:3695 (1990), results in the corresponding 1-thiophenyl derivative [4]. After elimination of the acetyl protective groups [5], the benzylidene group and the allyl group (benzaldehyde dimethyl acetal/CSA; allyl bromide/NaH) are introduced. Reduction with NaCNBH$_3$ results in liberation of the 4-OH group [6].

Synthesis of a protected galactose unit

Galactose [7] is converted by the procedure of Nicolaou et al., J. Chem. Soc.: Chem. Comm. 870 (1991), by mixing with acetic anhydride/triethylamine/ DMAP and tin tetrachloride/thiophenol into the thioglycoside [8]. After elimination of the acetyl protective groups, compound [9] is produced by reduction with benzaldehyde dimethyl acetal/CSA. Acetylation (acetic anhydride/triethylamine/ DMAP) followed by reduction with NaCNBH$_3$ results in compound [10]. After renewed acetylation (acetic anhydride/triethylamine/DMAP), the thioglycoside is converted by NBS/HF into the fluoride compound [11].

Synthesis of a protected fucose unit

Fucuse [15] is peracetylated (acetic anhydride/triethylamine/DMAP) by the procedure of Nicolaou et al., J. Am. Chem. Soc. 112:3694 (1990), and converted with tin tetrachloride/thiophenol into the thioglycoside [16]. Subsequently, after a replacement of the acetyl by benzyl protective groups (NaOMe/MeOH; NaH/BnBr), the thiophenol is converted with NBS/HF or NBS/DAST into the fluoride compound [17].

5,470,843
Scheme 1
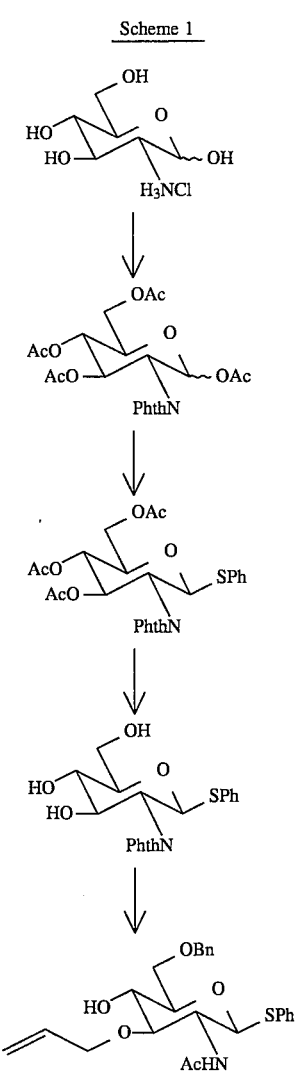
Scheme 2
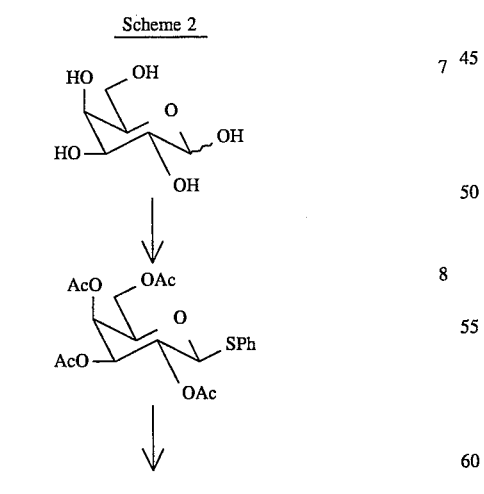
-continued
Scheme 2
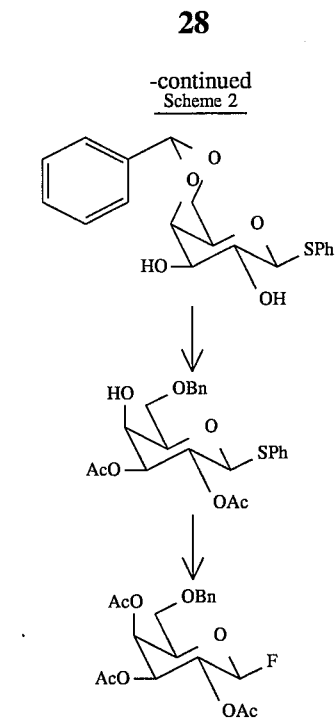
Scheme 3
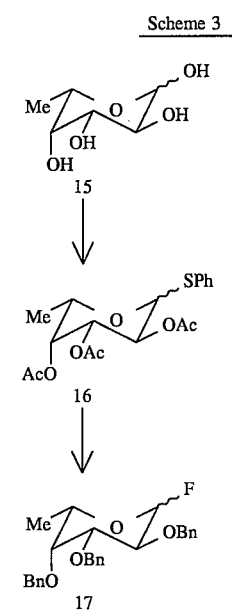
Scheme 4
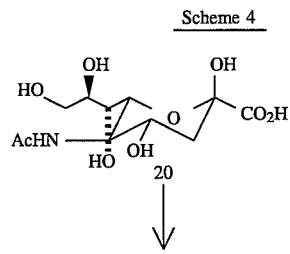

-continued
Scheme 4
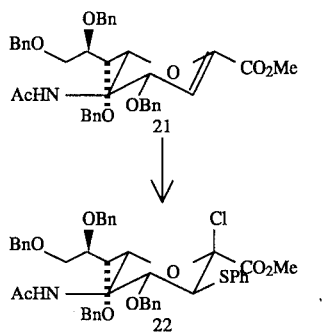
Scheme 5
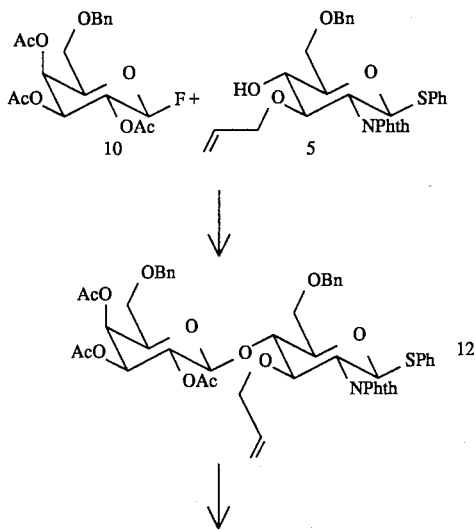
-continued
Scheme 5
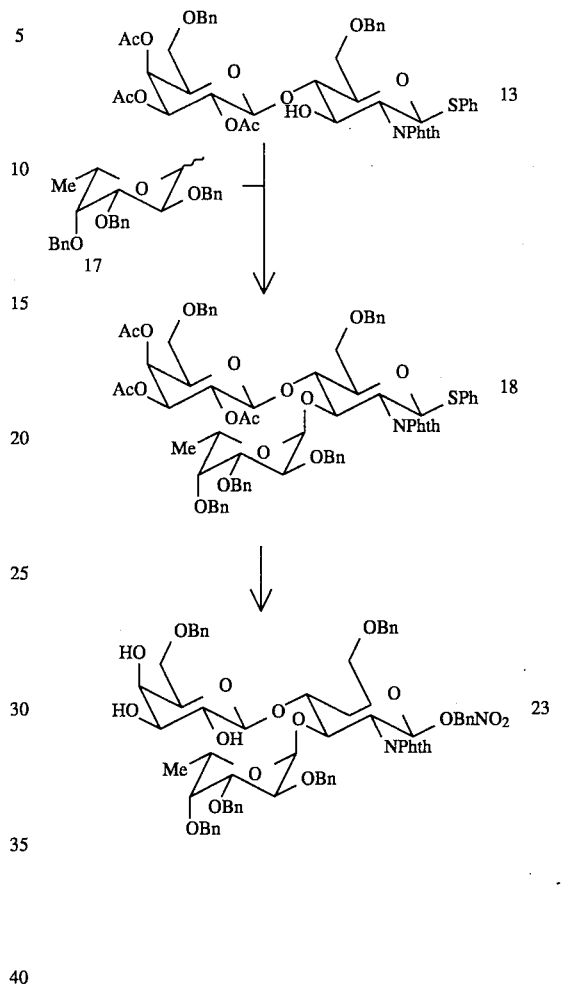
Scheme 6
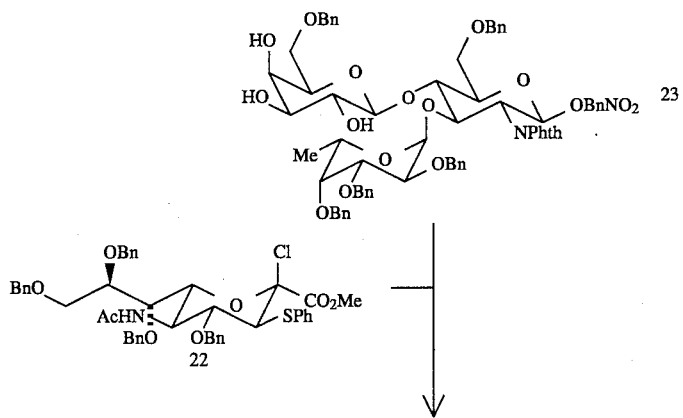

-continued
Scheme 6
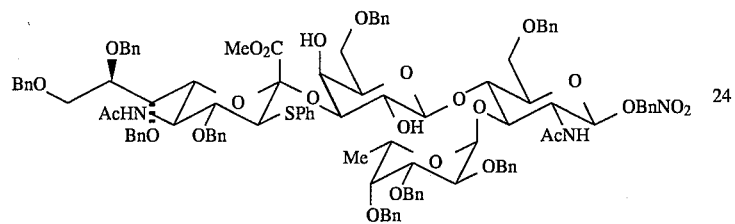
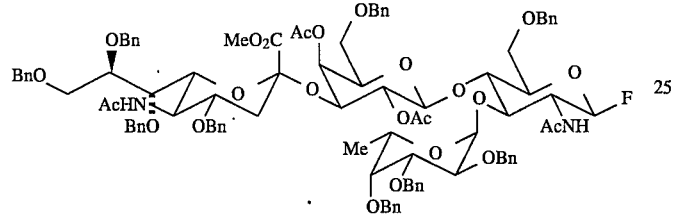
Scheme 7
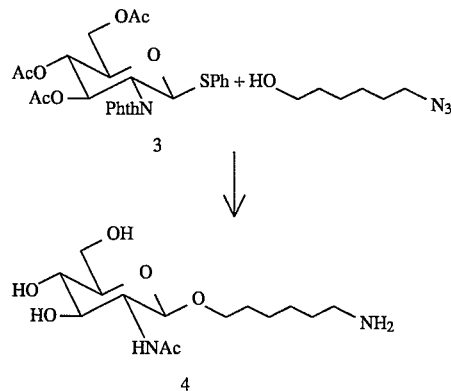
-continued
Scheme 7
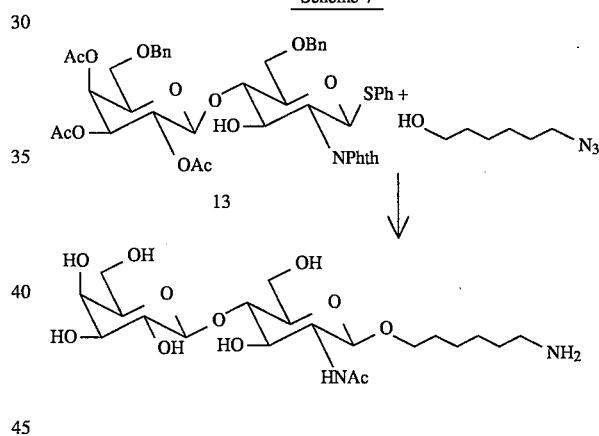
Scheme 8
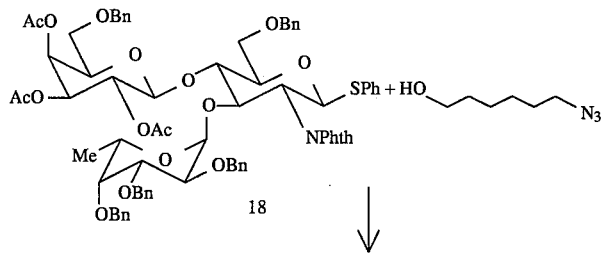

-continued
Scheme 8

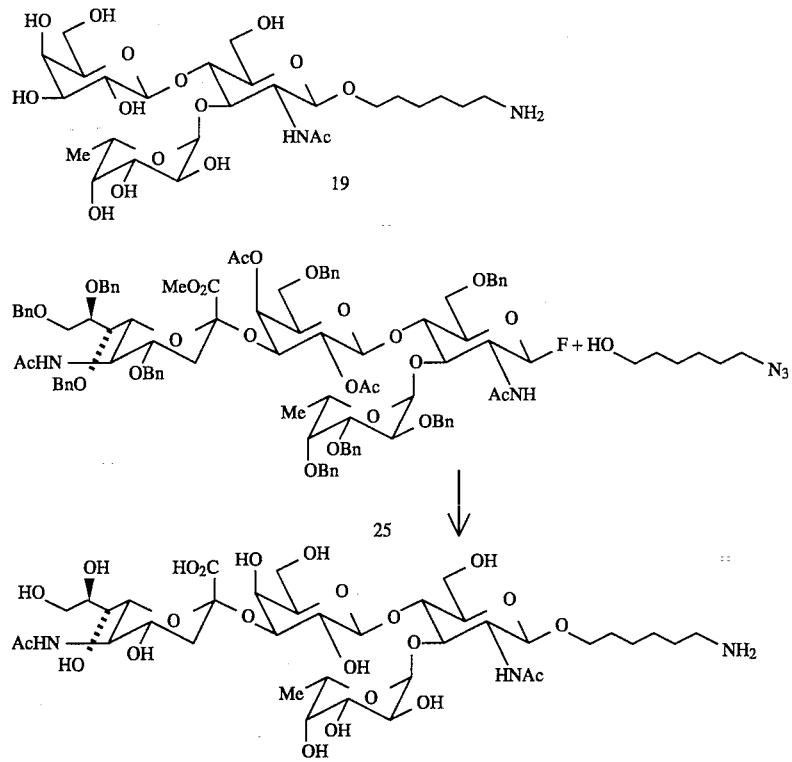

Synthesis of a Protected N-acetylneuraminic Acid Unit

N-Acetylneuraminic acid [20] is converted by treatment with Dowex 50 in methanol by the procedure of Kuhn et al., Chem. Ber. 99:611 (1966), into the corresponding methyl ester [15] and peracetylated with acetic anhydride in the presence of catalytic amounts of sulfuric acid by the procedure of Nicolaou et al., J. Chem. Soc.: Chem. Comm. 870 (1991). Subsequent deacetylation with sodium hydroxide solution and perbenzylation with benzyl bromide/NaOH/Bu$_4$NI gives compound [21]. Reaction with phenylsulfenyl chloride then results in the neuraminic acid donor [22].

Synthesis of the Protected N-acetyllactosamine Disaccharide

The galactosyl fluoride [11] is linked to the N-acetylglucosamine derivative [5] by the procedure of Nicolaou et al., J. Chem. Soc.: Chem. Comm. 870 (1991), in the presence of AgClO$_4$/SnCl$_2$ to give compound [12] which is converted by elimination of the allyl protective group (Ru(PPh$_3$)$_4$/H$_2$; TsOH/MeOH) into compound [13].

Synthesis of the Protected Lewis X Trisaccharide

The disaccharide [13] is reacted with the fucosyl fluoride [17] (AgClO$_4$/SnCl$_2$) by the procedure of Nicolaou et al. J. Chem. Soc.: Chem. Comm. 870 (1991), to give the Lewis X derivative [18].

Synthesis of the Protected Sialyl-Lewis X Tetrasaccharide

The trisaccharide [18] is converted by the procedure of Nicolaou et al. J. Am. Chem. Soc. 114:3127 (1992), with NBS/DAST into the fluoride which, after reaction with o-nitrobenzyl alcohol/AgClO$_4$/SnCl$_2$, yields the corresponding glycoside. Reaction with NaOMe/HOMe yields the trihydroxy compound [23]. The latter is linked by the trihydroxy compound [23]. The latter is linked by the procedure of Nicolaou et al. J. Am. Chem. Soc. 114:3127 (1992), by reaction with compound [22] in the presence of Hg(CN)$_2$/HgBr$_2$ to give the sialyl-Lewis X derivative [24].

In accordance with the procedure of Nicolaou et al., J. Am. Chem. Soc. 114:3127 (1992), acetylation is carried out with acetic anhydride/pyridine and the nitrobenzyl group is eliminated by irradiation. Subsequently the thiophenyl group is eliminated by reaction with triphenyltin hydride/AIBN, and conversion into the fluoride compound [25] takes place by reaction with diethylaminosulfur trifluoride. The latter compound is then reacted in analogy to the above procedure with 6-azidohexanol in the presence of AgOTf/HfCp$_2$Cl$_2$ to give the corresponding glycoside.

The elimination of the acetyl protective groups and that of the phthaloyl protective group takes place with hydrazine hydrate, and that of the methyl ester takes place with LiI/pyridine in analogy to the procedure of Nicolaou et al. J. Am. Chem. Soc. 114:3127 (1992). Before elimination of the benzyl protective groups H$_2$/Pd(OH)$_2$, MeOH), the free amino group is selectively acetylated in the presence of the free hydroxyl groups with excess acetic anhydride. The result is compound [26].

E5. Synthesis of Polymers.

The invention is illustrated further in the examples which follow. Percentage data relate to weight. Mixing ratios of liquids relate to volume unless otherwise indicated.

The biodegradable polymers suitable for coupling of mono-, di- and oligosaccharide units are prepared by described processes of polymer chemistry. The coupling itself takes place by conventional synthetic processes carried out on polymers. Thus, for example, poly-D,L-succinimide (PSI) is obtained by the procedure of Neri et al., J. Med. Chem. 16:893 (1973), by the action of 85% strength phosphoric acid on aspartic acid at temperatures of 160° C.–180° C. Reaction of PSI polymer with hydroxyethylamine at room temperature or slightly elevated temperature results in poly-$\alpha,\beta$-(2-hydroxyethyl)-D,L-aspartamide (PHEA). Id.

The alcohol groups in PHEA can be esterified by conventional processes (U.S. Pat. No. 5,041,291). Partial reaction of PSI with ethanolamine results in corresponding copolymers (U.S. Pat. No. 5,229,469). Basic hydrolysis of PSI leads to polyaspartic acid, by analogy to Giammona et al., *Chem. Pharm. Bull.* 37:2245 (1989). PSI can also be reacted with other amines in analogy to the reaction with hydroxyethylamine (EP 0 548 794), whereby it is possible to introduce additional functional groups which may act as potentiators.

Another starting polymer, poly-L-lysine methyl esterfumaramide, is prepared by boundary phase polycondensation from L-lysine methyl ester and fumaryl dichloride (U.S. Pat. No. 4,834,248). The methyl ester groups can be reacted, directly or after partial hydrolysis and subsequent activation, for example as p-nitrophenyl ester, with the mono-, di- and oligosaccharides containing amino groups.

Carbohydrate-containing polymers based on polyglutamates can be prepared analogously, i.e., by means of the p-nitrophenyl ester (polymer synthesis in analogy to Anderson, in *MACROMOLECULES AS DRUGS AND AS CARRIERS FOR BIOLOGICALLY ACTIVE MATERIALS*, D. A. Tirell (ed.) *N.Y. Acad. Sci.*, New York (1985), pages 67–75).

Hydroxyethylstarch is activated, before the reaction with the carbohydrate derivatives containing amino groups, by periodate oxidation (in analogy to Schacht et al., in *MACROMOLECULES AS DRUGS AND AS CARRIERS FOR BIOLOGICALLY ACTIVE MATERIALS*, D. A. Tirell (ed.), *N.Y. Acad. Sci.*, New York (1985), 199–212, or by reaction with chlorocarbonic esters such as p-nitrophenyl and N-hydroxysuccinimidyl chloroformates, by analogy to Wilchek and Miron, *Biochem. Int.* 4:629 (1982).

E6. Reaction Conditions for Polymer/Potentiator with Carbohydrate/Spacer Complex The reaction of the polymer with the potentiator on the one hand and of the carbohydrate portion with the bifunctional spacer on the other hand takes place in homogeneous solution, preferably in water or in water-miscible solvents such as, preferably, dimethylformamide or acetonitrile. Particularly preferably in a mixture of water and water-miscible solvents, preferably in the ratio 1:1. The reaction is carried out at 0° C.–80° C., preferably at 20°· C.–40° C. and particularly preferably at 35° C.–40° C. Numbers indicated in square brackets in the following examples relate to the numbers indicated in the schemes.

E7 Synthesis of the Monosaccharide.
E7.1 Synthesis of the Individual Sugar Units.
E7.1.1 Synthesis of the N-acetylglucosamine Unit.

1,3,4,6-Tetra-O-acetyl-2-deoxy-2-phthalimido-β-D-glucopyranose [2]

D-Glucosamine hydrochloride [1] (0.22–5.32 g, 1–20 mmol) is added to a solution of sodium methylate (prepared from 0.02–0.56 g of sodium and 1–20 ml of methanol), shaken for 10 min and filtered to removed precipitated sodium chloride. The filtrate is stirred with phthalic anhydride (0.07–1.48 g, 0.5–10 mmol) for 10 min and then triethylamine (0.10–2.02 g, 1–20 mmol) is added. After the reaction is complete, the solvent is evaporated and the residue is cooled and pyridine (2–40 ml) and acetic anhydride (5–20 ml) are added. After 16 h at room temperature, the mixture is poured into ice and the product is extracted with dichloromethane. Washing with water, dilute hydrochloric acid and saturated sodium bicarbonate solution results in the crude product which is recrystallized from ether (0.31–8.02 g, about 82% yield). FAB-MS: M+H$^+$=454. NMR data consistent with Lemieux et al., *ACS Symp. Ser.* 39:90 (1976).

1-Thiophenyl-3,4,6-tri-O-acetyl-2-deoxy-2-phthalimido-β-D-glucopyranose [3]

The product compound [2] (0.31–8.02 g, 0.68–17.7 mmol) is dissolved in 3.2–100 ml of dry dichloromethane, and thiophenol (0.15–3.9 g, 1.36–35.4 mmol) and tin tetrachloride (0.35–9.22 g, 1.36–35.4 mmol) are added and the mixture is stirred until reaction is complete. The reaction mixture is diluted and then washed with saturated sodium bicarbonate solution. Concentration results in the crude product compound [3]. Purification takes place by chromatography on silica gel with an ethyl acetate/isohexane gradient (0.27–71.4 g, 0.54–14.2 mmol, about 80%). FAB-MS: M+H$^+$=504. NMR data consistent with Nicolaou et al., *J. Am. Chem. Soc.* 112:3695 (1990) and T. J. Caulfield, Ph.D. Dissertation, the University of Pennsylvania (1991).

1-(6-Aminohexyl)-2-deoxy-2-acetamido-β-D-glucopyranose [4]

The crude product compound [3] (0.27–7.14 g, 0.54–14.2 mmol) and 6-azidohexanol (0.27–3.54 g, 1.08–14.1 mmol) are dissolved in dry acetonitrile, at 0° C., molecular sieves (0.2–5 g, 3 Å) and trimethylsilyl trifluoromethanesulfonate (0.02–1.56 g, 0.1–7 mmol) are added. After the reaction is complete, the mixture is filtered and washed with saturated sodium bicarbonate solution. Concentration results in the crude product, which is purified by chromatography on silica gel with an ethyl acetate/isohexane gradient (0.17–2.23 g, 0.35–4.58 mmol, about 69% yield). The product is then taken up in methanol/hydrazine hydrate (1:1) 1–30 ml) and heated at 80° C. until reaction is complete. After evaporation of the solvent, the crude product is taken up in dichloromethane/methanol (1:1) and stirred at 0° C. with acetic anhydride (3.5–45.8 mmol) until reaction is complete. After evaporation, the azide is reduced with hydrogen in the presence of catalytic amounts of palladium on carbon (10%) (0.01–1.5 g) in methanol (0.5–40 ml). The crude product resulting after evaporation is purified by gel chromatography on Biogel P2 (compound [4];0.08–1.02 g, 0.25–3.2 mmol, about 70% yield). FAB-MS: M+H$^+$=321. $^1$H-NMR [300 MHz, DMSO]: 7.68 (HNAc), 4.23 (GlcNAc-H-1), 3.78–3.6 (m), 3.49–3.23 (m), 3.08–3.02 (m) 2.58, 179 (GlcNCOC$\underline{H}_3$), 1.51–1.21 (O—(C$\underline{H}_2$)—N).
E8. Synthesis of the Disaccharide.
E8.1 Synthesis of the Individual Sugar Units.
E8.1.1 Synthesis of the N-acetylglucosamine Unit. [6].

1,3,4,6-Tetra-O-acetyl-2-deoxy-2-phthalimido-β-D-glucopyranose [2]

D-Glucosamine hydrochloride [1] (0.22–5.32 g, 1–20 mmol) is added to a solution of sodium methylate (prepared from 0.02–0.56 g of sodium and 1–20 ml of methanol), shaken for 10 min and filtered to removed precipitated sodium chloride. The filtrate is stirred with phthalic anhydride (0.07–1.48 g, 0.5–10 mmol) for 10 min and then triethylamine (0.10–2.02 g, 1–20 mmol) is added. After the reaction is complete, the solvent is evaporated and the residue is cooled and pyridine (2–40 ml) and acetic anhydride (5–20 ml) are added. After 16 h at room temperature, the mixture is poured into ice and the product is extracted with dichloromethane. Washing with water, dilute hydrochloric acid and saturated sodium bicarbonate solution results in the crude product which is recrystallized from ether (0.31–8.02 g, about 82% yield). FAB-MS: M+H⁺=454. NMR data consistent with Lemieux et al., *ACS Symp. Ser.* 39:90 (1976).

1-Thiophenyl-2-deoxy-2-phthalimido-β-D-glucopyranose [5]

The product compound [2] (0.31–8.02 g, 0.68–17.7 mmol) is dissolved in 3.2–100 ml of dry dichloromethane, and thiophenol (0.15–3.9 g, 1.36–35.4 mmol) and tin tetrachloride (0.35–9.22 g, 1.36–35.4 mmol) are added and the mixture is stirred until reaction is complete. The reaction mixture is diluted and then washed with saturated sodium bicarbonate solution. The crude product compound [3] obtained in this way is purified by chromatography on silica gel with an ethyl acetate/isohexane gradient (0.27–7.14 g, 0.54–14.2 mmol, about 80%) and is dissolved in anhydrous methanol (3–90 ml) and catalytic amounts of sodium methylate (prepared from 0.002–0.05 g of sodium in 0.1–2 ml of methanol) are added. After the reaction is complete, the mixture is neutralized with acetic ion exchanger (0.2–5 g Amberlite IR-120, H⁺-form) (compound [5]; 0.21–5.31 g, 0.54–14.1 mmol, about 99% yield). FAB-MS: M+H⁺=378. NMR data consistent with Nicolaou et al., *J. Am. Chem. Soc.* 112:3695 (1990) and T. J. Caulfield, Ph.D. Dissertation, the University of Pennsylvania (1991).

1-Thiophenyl-3-O-allyl-6-O-benzyl-2-deoxy-2-phthalimido-β-D-glucopyranose [6]

The crude product compound [5] (0.21–5.31 g, 0.54–14.1 mmol) is stirred in anhydrous acetonitrile (3–90 ml) with benzaldehyde dimethyl acetal (0.12–3.22 g, 0.81–21.1 mmol) and catalytic amounts of p-toluenesulfonic acid (4–90 mg) until the reaction is finished. The crude product resulting after washing with saturated sodium bicarbonate solution is taken up in anhydrous dimethylformamide (2.5–85 ml), and sodium hydride (0.02–0.51 g, 0.81–21.15 mmol) and allyl bromide (0.09–2.37 g, 0.75–19.74 mmol) are added. After the reaction is complete, methanol (0.06–1.55 ml, 2.7–70.5 mmol) is added, and the mixture is diluted with ethyl acetate and washed successively with saturated ammonium chloride and saturated sodium bicarbonate solution. The crude product compound [5] is purified by chromatography under silica gel with an ethyl acetate/isohexane gradient (0.23–5.98 g, 0.46–12.13 mmol, about 86%) and subsequently taken up in dry tetrahydrofuran (3.5–90 ml), and sodium cyanoborohydride (0.67–17.7 g, 10.8–282 mmol) is added. Subsequently, ethereal hydrochloric acid solution is slowly added until reaction is complete. After filtration, the organic phase is diluted with ethyl acetate and washed with saturated sodium bicarbonate solution to neutrality. The crude product compound [6] is purified by chromatography on silica gel with an ethyl acetate/isohexane gradient (0.17–4.56 g 0.35–9.17 mmol, about 74% yield). FAB-MS: M+H⁺=416. NMR data consistent with Nicolaou et al., *J. Am. Chem. Soc.* 112:3695 (1990) and T. J. Caulfield, Ph.D. Dissertation, The University of Pennsylvania (1991).

E8.1.2 Synthesis of the Galactose Unit [11].

1-Thiophenyl-2,3,4,6-tetra-O-acetylgalacto-β-D-pyranose [8]

Galactose [7] (0.18–3.6 g, 1–20 mmol) is suspended in dichloromethane (5–90 ml), and acetic anhydride (0.75–15.43 g, 7.5–150 mmol), triethylamine (0.8–16.3 g, 8–160 mmol) and catalytic amounts of dimethylaminopyridine (0.01–0.1 g) are added. After the reaction is complete, the mixture is poured into ice-water and the product is extracted with dichloromethane. The crude product obtained by washing the extract with dilute hydrochloric acid and saturated sodium bicarbonate solution is dissolved in dry dichloromethane (3.5–110 ml), and thiophenol (0.22–4.41 g, 2–40 mmol) and tin tetrachloride (0.51–10.28 g, 2–40 mmol) are added. After the reaction is complete, the mixture is diluted, and washing with saturated sodium bicarbonate solution results in the crude product compound [8] which is purified by chromatography on silica gel with an ethyl acetate/isohexane gradient (0.37–7.48 g, 0.85–17 mmol, about 85% yield). FAB-MS: M+H⁺=441. NMR data consistent with Nicolaou et al., *J. Am. Chem. Soc.* 112:3695 (1990) and T. J. Caulfield, Ph.D. Dissertation, The University of Pennsylvania (1991).

1-Thiophenyl-4,6-O-benzylidene-β-D-galactopyranose [9]

The product compound [8] (0.37–7.48 g, 0.85–17 mmol) is dissolved in anhydrous methanol (4–150 ml), and catalytic amounts of sodium methylate (prepared from 0.003–0.06 g of sodium in 0.1–2.5 ml of methanol) are added. After the reaction is complete, the mixture is neutralized with an acidic ion exchanger (0.25–6 g Amberlite IR-120, H⁺-form) and evaporated. The resulting reaction product is stirred in anhydrous acetonitrile (4.5–150 ml) with benzaldehyde dimethyl acetal (0.19–5.05 g, 1.27–33.1 mmol) and catalytic amounts of p-toluenesulfonic acid (4–90 mg) until the reaction is finished. Washing with saturated sodium bicarbonate solution results in the crude product compound [9] which is purified by chromatography on silica gel with a dichloromethane/methanol gradient (0.28–5.51 g, 0.77–15.3 mmol, about 90% yield). FAB-MS: M+H⁺=361. NMR data consistent with Nicolaou et al., *J. Am. Chem. Soc.* 114:3127 (1992) and C. W. Hummel, Ph.D. Dissertation, University of California, San Diego (1993).

1-Thiophenyl-2,3-di-O-acetyl-6-O-benzyl-β-D-galactopyranose [10]

Product compound [9] (0.28–5.51 g, 0.77–15.3 mmol) is suspended in dichloromethane (4–60 ml), and acetic anydride (0.23–4.75 g, 2–40 mmol), triethylamine (0.25–5.02 g, 2.46–49.23 mmol) and catalytic amounts of dimethylaminopyridine (0.01–0.08 g) are added. After the reaction is complete, the mixture is poured into ice-water and the product is extracted with dichloromethane.

The crude product obtained by washing the extract with dilute hydrochloric acid and saturated sodium bicarbonate solution is dissolved in dry tetrahydrofuran (2.45–130 ml), and sodium cyanoborohydride (0.96–25.3 g, 15.4–402.8 mmol) is added. Subsequently ethereal hydrochloric acid solution is added slowly until the reaction is complete. After filtration, the organic phase is diluted with ethyl acetate and washed with saturated sodium bicarbonate solution to neutrality. The crude product compound [10] is purified by chromatography on silica gel with an ethyl acetate/isohexane gradient (0.27–5.46 g, 0.62–12.24 mmol, about 80% yield). FAB-MS: M+H⁺=447. NMR data consistent with Nicolaou et al., *J. Am. Chem. Soc.* 114:3127 (1992) and C. W. Hummel, Ph.D. Dissertation, University of California, San Diego (1993).

1-Fluoro-2,3,4-tri-O-acetyl-6-O-benzyl-β-D-galactopyranose [11]

The product compound [9] (0.27–5.46 g, 0.62–12.24 mmol) is suspended in dichloromethane (4–60 ml) and acetic anhydride (0.14–2.91 g, 1.24–24.8 mmol), triethylamine (0.15–3.11 g, 1.53–30.53 mmol) and catalytic amounts of dimethylaminopyridine (0.003–0.04 g) are added. After the reaction is complete, the mixture is poured into ice-water and the product is extracted with dichloromethane. The crude product obtained by washing the extract with dilute hydrochloric acid and saturated sodium bicarbonate solution is taken up in dry dichloromethane (5–80 ml) and, at −78° C., dimethylaminosulfur trifluoride (0.25–4.89 g, 1.86–36.7 mmol) and N-bromosuccinimide (0.11–3.26 g, 0.93–18.36 mmol) are added, and the mixture is warmed to room temperature. After washing with saturated sodium bicarbonate solution, the mixture is concentrated and the byproducts of the reaction are removed by silica gel chromatography (stepwise gradient: ethyl acetate/isohexane) to produce compound [11] (0.21–4.14 g, 0.53–10.4 mmol, about 85% yield). FAB-MS: M+H$^+$=399. NMR data consistent with Nicolaou et al., *J. Am. Chem. Soc.* 114:3127 (1992) and C. W. Hummel, Ph.D. Dissertation, University of California, San Diego (1993).

E8.2 Assembly of the Disaccharide from the N-acetylglucosamine Unit and the Galactose Unit.

1-Thiophenyl-(2,3,4-tri-O-acetyl-6-O-benzyl-β-D-galactopyranosyl)-(1-4)-3-O-alkyl-2-deoxy-2-acetamido-β-D-glucopyranose [12]

The N-acetylglucosamine derivative [5] (0.17–4.56 g, 0.35–9.17 mmol) and the galactose derivative [11] (0.21–4.14 g, 0.53–10.4 mmol) are dissolved in dichloromethane (3–120 ml) and, at 0° C., 4 Å molecular sieves (0.15–7.8 g), silver perchlorate (0.11–5.39, 0.525–26.0 mmol) and tin (II) chloride (0.1–4.93 g, 0.525–26.0 mmol) are added. After the reaction is complete, the mixture is filtered and washed with saturated sodium bicarbonate solution. The crude product compound [12] is purified by chromatography on silica gel with an ethyl acetate/isohexane gradient (0.23–5.61 g 0.26–6.42 mmol, about 70% yield). FAB-MS: M+H$^+$=874. NMR data consistent with Nicolaou et al., *J. Am. Chem. Soc.* 114:3127 (1992) and C. W. Hummel, Ph.D. Dissertation, University of California, San Diego (1993).

1-Thiophenyl-(2,3,4-tri-O-acetyl-6-O-benzyl-β-D-galactopyranosyl)-(1-4)-2-deoxy-2-acetamido-β-D-glucopyranose [13]

Compound [12] (0.23–5.61 g, 0.26–6.42 mmol) is dissolved in ethanol (30–900 ml) and heated at 95° C. with catalytic amounts of tetrakis(triphenylphosphine)-ruthenium(II) hydride (0.005–0.04 g). After the reaction is complete, the mixture is filtered, concentrated and taken up in methanol (2.5–85 ml) and catalytic amounts of p-toluenesulfonic acid (0.001–0.08 g) are added. After the reaction is complete, the mixture is washed with saturated sodium bicarbonate solution and, after concentration, the crude product compound [13] is obtained. Purification takes place by chromatography on silica gel with an ethyl acetate/isohexane gradient (0.2–4.81 g, 0.234–5.78 mmol, about 90% yield). FAB-MS: M+H$^+$=834. NMR data consistent with Nicolaou et al., *J. Am. Chem. Soc.* 114:3127 (1992) and C. W. Hummel, Ph.D. Dissertation, University of California, San Diego (1993).

1-(6-Aminohexyl)-O-(β-D-galactopyranosyl)-(1-4)-2-deoxy-2-acetamido-β-D-glucopyranose [14]

Compound [13] (0.21–2.66 g, 0.54–7.05 mmol) and 6-azidohexanol (0.27–3.54 g, 1.08–14.1 mmol) are dissolved in dry acetonitrile and, at 0° C., molecular sieves (0.2–5 g) and trimethylsilyl trifluoromethanesulfonate (0.02–1.56 g, 1–70 mmol) are added. After the reaction is complete, the mixture is filtered and washed with saturated sodium bicarbonate solution. Concentration results in the crude product which is purified by chromatography on silica gel with an ethyl acetate/isohexane gradient (0.17–2.23 g, 0.35–4.58 mmol, about 65% yield). The product is subsequently taken up in methanol/hydrazine hydrate (1:1) (1–30 ml) and heated at 80° C. until reaction is complete. After evaporation of the solvent, the crude product is taken up in dichloromethane/methanol (1:1) and stirred at 0° C. with acetic anhydride (3.5–45.8 mmol) until reaction is complete. Evaporation is followed by reduction of the azide with hydrogen in the presence of catalytic amounts of palladium on carbon (10%) (0.01–1.5 g) in methanol (0.5–40 ml). The crude product compound [14] obtained after evaporation is purified by gel chromatography on Biogel P2 (0.12–1.54 g, 0.25–3.2 mmol, about 70% yield). FAB-MS: M+H$^+$=483. $^1$H-NMR [300 MHz, D$_2$O]: 4.98 (Fuc-$\underline{H}$-1), 4.28 (Gal-$\underline{H}$-1), 4.33, 3.99–3.38 (m), 2.99, 2.09 (GlcNCOC$\underline{H}_3$), 1.72–1.32 (O—(C$\underline{H}_2$)$_5$—CH$_2$—N), 1.11 (Fuc-C$\underline{H}_3$) ppm.

E9. Synthesis of the Trisaccharide.
E9.1 Synthesis of the Individual Sugar Units.
E9.1.1 Synthesis of the N-acetylglucosamine Unit [6]

1,3,4,6-Tetra-O-acetyl-2-deoxy-2-phthalimido-β-D-glucopyranose [2]

D-Glucosamine hydrochloride [1] (0.216–5.32 g, 1–20 mmol) is added to a solution of sodium methylate (prepared from 0.023–0.56 g) of sodium and 1–20 ml of methanol), shaken for 10 min and filtered to remove precipitated sodium chloride. The filtrate is stirred with phthalic anhydride (0.074–1.48 g, 0.5–10 mmol) for 10 min and then triethylamine (0.1–2.02 g, 1–20 mmol) is added. After the reaction is complete, the solvent is evaporated and the residue is cooled and pyridine (2–40 ml) and acetic anhydride (5–20 ml) are added. After 16 h at room temperature, the mixture is poured into ice and the product is extracted with dichloromethane. Washing with water, dilute hydrochloric acid and saturated sodium bicarbonate solution results in the crude product which is recrystallized from ether (0.31–8.02 g, about 82% yield). FAB-MS: M+H$^+$=454. NMR data consistent with Lemieux et al., *ACS Symp. Ser.* 39:90 (1976).

1-Thiophenyl-2-deoxy-2-phthalimido-β-D-glucopyranose [5]

Compound [2] (0.31–8.02 g, 0.68–17.7 mmol) is dissolved in 3.2–100 ml of dry dichloromethane, and thiophenol (0.15–3.9 g, 1.36–35.4 mmol) and tin tetrachloride 0.35–9.22 g, 1.36–35.4 mmol) are added and the mixture is stirred until reaction is complete. The reaction mixture is diluted and then washed with saturated sodium bicarbonate solution. The crude product compound [3] obtained in this way is purified by chromatography on silica gel with an ethyl acetate/isohexane gradient (0.27–7.14 g, 0.54–14.2 mmol, about 80%) and is dissolved in anhydrous methanol (3–90 ml) and catalytic amounts of sodium methylate (prepared from 0.002–0.05 g of sodium in 0.1–2 ml of methanol) are added. After the reaction is complete, the mixture is neutralized with an acidic ion exchanger (0.2–5 g Amberlite IR-120, H⁺-form) (4: 0.21–5.31 g, 0.54–14.1 mmol, about 99% yield). FAB-MS: M+H⁺=378. NMR data consistent with Nicolaou et al., *J. Am. Chem. Soc.* 112:3695 (1990)) and T. J. Caulfield, Ph. D. Dissertation, The University of Pennsylvania (1991).

1-Thiophenyl-3-O-allyl-6-O-benzyl-2-deoxy-2-phthalimido-β-D-glucopyranose [6]

The crude product compound [5] (0.21–5.31 g, 0.54–14.1 mmol) is stirred in anhydrous acetonitrile (3–90 ml) with benzaldehyde dimethyl acetal (0.12–3.22 g, 0.81–21.1 mmol) and catalytic amounts of p-toluenesulfonic acid (4–90 mg) until the reaction is finished. The crude product resulting after washing with saturated sodium bicarbonate solution is taken up in anhydrous dimethylformamide (2.5–85 ml), and sodium hydride (0.02–0.51 g, 0.81–21.15 mmol) and allyl bromide (0.09–2.37 g, 0.75–19.74 mmol) are added. After the reaction is complete, methanol (0.06–1.55 ml, 2.7–70.5 mmol) is added, and the mixture is diluted with ethyl acetate and washed successively with saturated ammonium chloride and saturated sodium bicarbonate solution. The crude product compound [5] is purified by chromatography on silica gel with an ethyl acetate/isohexane gradient (0.23–5.98 g, 0.46–12.13 mmol, about 86%) and subsequently taken up in dry tetrahydrofuran (3.5–90 ml), and sodium cyanoborohydride (0.67–17.7 g, 10.8–282 mmol) is added. Subsequently, ethereal hydrochloric acid solution is slowly added until reaction is complete. After filtration, the organic phase is diluted with ethyl acetate and washed with saturated sodium bicarbonate solution to neutrality. The crude product compound [6] is purified by chromatography on silica gel with an ethyl acetate/isohexane gradient (0.17–4.56 g, 0.35–9.17 mmol, about 74% yield). FAB-MS: M+H⁺=416. NMR data consistent with Nicolaou et al., *J. Am. Chem. Soc.* 112:3695 (1990) and T. J. Caulfield, Ph.D. Dissertation, The University of Pennsylvania (1991).

E9.1.2 Synthesis of the Galactose Unit [11].

1-Thiophenyl-2,3,4,6-tetra-O-acetyl-β-D-galactopyranose [8]

Galactose [7] (0.18–3.6 g, 1–20 mmol) is suspended in dichloromethane (5–90 ml), and acetic anhydride (0.75–15.43 g, 7.5–150 mmol), triethylamine (0.8–16.3 g, 8–160 mmol) and catalytic amounts of dimethylaminopyridine (0.01–0.1 g) are added. After the reaction is complete, the mixture is poured into ice-water and the product is extracted with dichloromethane. The crude product obtained by washing the extract with dilute hydrochloric acid and saturated sodium bicarbonate solution is dissolved in dry dichloromethane (3.5–110 ml), and thiophenol (0.22–4.41 g, 2–40 mmol) and tin tetrachloride (0.51–10.28 g, 2–40 mmol) are added. After the reaction is complete, the mixture is diluted, and washing with saturated sodium bicarbonate solution results in the crude product compound [8] which is purified by chromatography on silica gel with an ethyl acetate/isohexane gradient (0.374–7.48 g, 0.85–17 mmol, about 85% yield). FAB-MS: M+H⁺=441. NMR data consistent with Nicolaou et al., *J. Am. Chem. Soc.* 112:3695 (1990) T. J. Caulfield, Ph.D. Dissertation, The University of Pennsylvania (1991).

1-Thiophenyl-4,6-O-benzylidene-β-D-galactopyranose [9]

Compound [8] (0.374–7.48 g, 0.85–17 mmol) is dissolved in anhydrous methanol (4–150 ml), and catalytic amounts of sodium methylate (prepared from 0.003–0.06 g of sodium in 0.1–2.5 ml of methanol) are added. After the reaction is complete, the mixture is neutralized with an acidic ion exchanger (0.25–6 g Amberlite IR-120, H⁺-form) and evaporated. The resulting reaction product is stirred in anhydrous acetonitrile (4.5–150 ml) with benzaldehyde dimethyl acetal (0.19–5.05 g, 1.27–33.1 mmol) and catalytic amounts of p-toluenesulfonic acid (4– 90 mg) until the reaction is finished. Washing with saturated sodium bicarbonate solution results in the crude product compound [9] (0.28–5.51 g, 0.77–15.3 mmol, about 90% yield). FAB-MS: M+H⁺=361. NMR data consistent with Nicolaou et al., *J. Am. Chem. Soc.* 114:3127 (1992) and C. W. Hummel, Ph.D. Dissertation, University of California, San Diego (1993).

1-Thiophenyl-2,3-di-O-acetyl-6-O-benzyl-β-D-galactopyranose [10]

Compound [9] (0.28–5.51 g, 0.77–15.3 mmol) is suspended in dichloromethane (4–60 ml), and acetic anhydride (0.23–4.75 g, 2–40 mmol), triethylamine (0.25–5.02 g, 2.46–49.23 mmol) and catalytic amounts of dimethylaminopyridine (0.01–0.08 g) are added. After the reaction is complete, the mixture is poured into ice-water and the product is extracted with dichloromethane. The crude product obtained by washing the extract with dilute hydrochloric acid and saturated sodium bicarbonate solution is dissolved in dry tetrahydrofuran (2.45–130 ml), and sodium cyanoborohydride (0.96–25.3 g, 15.4–402.8 mmol) is added. Subsequently ethereal hydrochloric acid solution is added slowly until the reaction is complete. After filtration, the organic phase is diluted with ethyl acetate and washed with saturated sodium bicarbonate solution to neutrality. The crude product compound [10] is purified by chromatography on silica gel with an ethyl acetate/isohexane gradient (0.27–5.46 g, 0.62–12.24 mmol, about 80% yield). FAB-MS: M+H⁺=447. NMR data consistent with Nicolaou et al., *J. Am. Chem. Soc.* 114:3127 (1992) and C. W. Hummel, Ph. D. Dissertation, University of California, San Diego (1993).

1-Fluoro-2,3,4-tri-O-acetyl-6-O-benzyl-β-D-galactopyranose [11]

Compound [9] (0.27–5.46 g, 0.62–12.24 mmol) is suspended in dichloromethane (4–60 ml) and acetic anhydride (0.14–2.91 g, 1.24–24.8 mmol), triethylamine (0.15–3.11 g, 1.53–30.53 mmol) and catalytic amounts of dimethylaminopyridine (0.003–0.04 g) are added. After the reaction is complete, the mixture is poured into ice-water and the product is extracted with dichloromethane. The crude product obtained by washing the extract with dilute hydrochloric acid and saturated sodium bicarbonate solution is taken up in dry dichloromethane (5–80 ml) and, at −78° C., dimethylaminosulfur trifluoride (0.25–4.89 g) and N-bromosuccinimide (0.11–3.26 g 0.93–18.36 mmol) are added, and the mixture is warmed to room temperature. After washing with saturated sodium bicarbonate solution, the mixture is concentrated and the byproducts of the reaction are removed by silica gel chromatography (stepwise gradient: ethyl acetate/isohexane) to produce compound [11] (0.21–4.14 g, 0.53–10. mmol, about 85% yield). FAB-MS: M+H⁺=399. NMR data consistent with Nicolaou et al., *J. Am. Chem. Soc.* 114:3127 (1992) and C. W. Hummel, Ph.D. Dissertation, University of California, San Diego (1993).

E9.1.3 Synthesis of the Fucose Unit [17].

1-Thiophenyl-2,3,4-tri-O-acetyl-β-L-fucose [16]

Fucose [15] (0.16–32.8 g, 1–20 mmol) is suspended in dichloromethane (5–90 ml), and acetic anhydride (0.75–15.43 g, 7.5–150 mmol), triethylamine (0.8–16.3 g, 8–160 mmol) and catalytic amounts of dimethylaminopyridine (0.01–0.1 g) are added. After the reaction is complete, the mixture is poured into ice-water and the product is extracted with dichloromethane. The crude product obtained by washing the extract with dilute hydrochloric acid and saturated sodium bicarbonate solution is dissolved in dry dichloromethane (3.5–110 ml), and thiophenol (0.22–4.41 g, 2–40 mmol) and tin tetrachloride (0.51–10.28 g, 2–40 mmol) are added. After the reaction is complete, the mixture is diluted, and washing with saturated sodium bicarbonate solution results in the crude product compound [16] which is purified by chromatography on silica gel with an ethyl acetate/isohexane gradient (0.34–6.88 g, 0.9–18 mmol, about 90% yield). FAB-MS: M+H$^+$=382. NMR data consistent with Nicolaou et al., *J. Am. Chem. Soc.* 112:3695 (1990) and T. J. Caulfield, Ph.D. Dissertation, The University of Pennsylvania (1991).

1-Thiophenyl-2,3,4-tri-O-benzyl-β-L-fucose [17]

Compound [16] (0.34–6.88 g, 0.9–18 mmol) is dissolved in anhydrous methanol (5–180 ml), and catalytic amounts of sodium methylate (prepared from 0.005–0.009 g of sodium in 0.2–2.9 ml of methanol) are added. After the reaction is complete, the mixture is neutralized with an acidic ion exchanger (0.3–6.7 g Amberlite IR-120, H$^+$-Form) and evaporated. The resulting reaction product is taken up in anhydrous dimethylformamide (5–140 ml) and sodium hydride (0.16–3.21 g, 6.75–135 mmol) and benzyl bromide (0.92–18.46 g, 5.4–108 mmol) are added. After the reaction is complete, methanol (0.16–3.2 g, 5–100 mmol) is added, and the mixture is diluted with ethyl acetate and washed successively with saturated ammonium chloride and saturated sodium bicarbonate solution. The crude product after chromatography on silica gel (ethyl acetate/isohexane gradient) is subsequently taken up in dry dichloromethane (8–120 mol) and, at −78° C., dimethylaminosulfur trifluoride (0.36–7.09 g, 2.69–53.18 mmol) and N-bromosuccinimide (0.16–4.73 g, 1.35–26.6 mmol) are added, and the mixture is warmed to room temperature. After washing with saturated sodium bicarbonate solution, the mixture is concentrated, and the byproducts of the reaction are removed by silica gel chromatography (stepwise gradient: ethyl acetate/isohexane) to result in compound [17] (0.33–6.47 g, 0.72–14.4 mmol, about 80% yield). FAB-MS: M+H$^+$=450. NMR data consistent with Nicolaou et al., *J. Am. Chem. Soc.* 112:3695 (1990) and T. J. Caulfield, Ph.D. Dissertation, the University of Pennsylvania (1991).

E9.2 Assembly of the Disaccharide from the N-acetylglucosamine Unit and the Galactose Unit.

1-Thiophenyl-(2,3,4-tri-O-acetyl-6-O-benzyl-β-D-galactopyranosyl)-(1-4)-3-O-alkyl-2-deoxy-2-acetamido-β-D-glucopyranose [12]

The N-acetylglucosamine derivative [5] (0.17– 4.56 g, 0.35–9.17 mmol) and the galactose derivative [11] (0.21–4.14 g, 0.53–10.4 mmol) are dissolved in dichloromethane (3–120 ml) and, at 0° C., 4 Å molecular sieves (0.15–7.8 g), silver perchlorate (0.11–5.39, 0.525–26.0 mmol) and tin(II) chloride (0.1–4.93 g, 0.525–26 mmol) are added. After the reaction is complete, the mixture is filtered and washed with saturated sodium bicarbonate solution. The crude product compound [12] is purified by chromatography on silica gel with an ethyl acetate/isohexane gradient (0.23–5.61 g, 0.26–6.42 mmol, about 70% yield). FAB-MS: M+H$^+$=874. NMR data consistent with Nicolaou et al., *J. Am. Chem. Soc.* 114:3127 (1992)) and C. W. Hummel, Ph.D. Dissertation, University of California, San Diego (1993).

1-Thiophenyl-(2,3,4-tri-O-acetyl-6-O-benzyl-β-D-galactopyranosyl)-(1-4)-2-acetamido-β-D-glucopyranose [13]

Compound [12] (0.23–5.61 g, 0.26–6.42 mmol) is dissolved in ethanol (3–90 ml) and heated at 95° C. with catalytic amounts of tetrakis(triphenylphosphine)-ruthenium(II) hydride (0.005–0.04 g). After the reaction is complete, the mixture is filtered, concentrated and taken up in methanol (2.5–85 ml) and catalytic amounts of p-toluenesulfonic acid (0.001–0.08 g) are added. After the reaction is complete, the mixture is washed with saturated sodium bicarbonate solution and, after concentration, the crude product compound [13] is obtained. Purification takes place by chromatography on silica gel with an ethyl acetate/isohexane gradient (0.2–4.81 g, 0.234–5.78 mmol, about 90% yield). FAB-MS: M+H$^+$=834. NMR data consistent with Nicolaou et al., *J. Am. Chem. Soc.* 114:3127 (1992) and C. W. Hummel, Ph.D. Dissertation, University of California, San Diego (1993).

E9.3 Assembly of the Trisaccharide from the Disaccharide and the Fucose Unit.

1-Thiophenyl-(2,3,4-tri-O-acetyl-6-O-benzyl-β-D-galactopyranosyl)-1-4)-[(2,3,4-tri-O-benzyl-α-L-fucopyranosyl)-(1-3)]-2-deoxy-2-acetamido-β-D-glucopyranose [18]

Compound [13] (0.2–4.81 g, 0.234–5.78 mmol) is dissolved with compound [17] (0.17–4.15 g, 0.37–9.25 mmol) in dry diethyl ether (5–100 ml) and stirred with 4 Å molecular sieves (0.1–6.8 g), silver perchlorate (0.15–3.59 g, 0.702–17.34 mmol) and tin(II) chloride (0.13–3.29 g, 0.702–17.34 mmol) until the reaction is complete. The mixture is subsequently filtered, and the crude product compound [18] obtained after concentration is purified by chromatography on silica gel with an ethyl acetate/isohexane gradient (0.25–6.2 g, 0.2–4.91 mmol, about 85% yield). FAB-MS: M+H$^+$=1262. NMR data consistent with Nicolaou et al., *J. Am. Chem. Soc.* 114:3127 (1992) and C. W. Hummel, Ph.D. Dissertation, University of California, San Diego (1993).

1-(6-Aminohexyl)-O-[(-β-D-galactopyranosyl)-(1-4)]-O-[(α-L-fucopyranosyl)-(1-3)-]-2-deoxy-2-acetamido-β-D-glucopyranose [19]

Compound [18] (0.25–6.2 g, 0.2–4.91 mmol) and 6-azidohexanol (0.11–2.47 g, 0.4–9.82 mmol) are dissolved in dry acetonitrile and, at 0° C., 3 Å molecular sieves (0.1–2.5 g) and trimethylsilyl trifluoromethanesulfonate (0.01–0.78 g, 0.02–7 mmol) are added. After the reaction is complete, the mixture is filtered and washed with saturated sodium bicarbonate solution. Concentration results in the crude product which is purified by chromatography on silica gel with an ethyl acetate/isohexane gradient (0.18–4.48 g, 0.13–3.19 mmol, about 65% yield). It is subsequently taken up in methanol/hydrazine hydrate (1:1) (1–50 ml) and heated at 80° C. until reaction is complete. After evaporation of the solvent, the crude product is taken up in dichloromethane/methanol (1:1) and stirred at 0° C. with acetic anhydride (1.3–40 mmol) until reaction is complete. Evaporation is followed by reduction of the azide with hydrogen in the presence of catalytic amounts of palladium on carbon (10%) (0.01–1.5 g) in methanol (0.5–35 ml). The crude product compound [19] obtained after evaporation is purified by gel chromatography on Biogel P2 (0.06–1.35 g, 0.09–2.23 mmol, about 70% yield). FAB-MS: M+H$^+$=608. $^1$H-NMR [300 MHz, DMSO]: 7.98 (N$\underline{H}_3$$^+$OAc$^-$), 4.92 (Fuc-$\underline{H}$-1), 4.65 ($\underline{H}$NAc), 4.36 (GlcNAc-$\underline{H}$-1), 4.28 (Gal-$\underline{H}$-1), 4.1–3.35 (m), 3.26 (C$\underline{H}_2$—NH$_3$$^+$OAc$^-$), 1.79 (GlcNCOC$\underline{H}_3$) 1.58–1.18 (O—(C$\underline{H}_2$)$_5$—CH$_2$—NH$_3$$^+$OAc$^-$), 0.99 (Fuc-C$\underline{H}_3$) ppm.

E10. Synthesis of the Tetrasaccharide.
E10.1 Synthesis of the Individual Sugar Units.
E10.1.1 Synthesis of the N-acetylglucosamine Unit. [6]

1,3,4,6-Tetra-O-acetyl-2-deoxy-2-phthalimido-β-D-glucopyranose [2]

D-Glucosamine hydrochloride [1] (0.216–5.32 g, 1–20 mmol) is added to a solution of sodium methylate (prepared from 0.023–0.56 g of sodium and 1–20 ml of methanol), shaken for 10 min and filtered to remove precipitated sodium chloride. The filtrate is stirred with phthalic anhydride (0.074–1.48 g, 0.5–10 mmol) for 10 min and then triethylamine (0.1–2.02 g, 1–20 mmol) is added. After the reaction is complete, the solvent is evaporated and the residue is cooled and pyridine (2–40 ml) and acetic anhydride (5–20 ml) are added. After 16 h at room temperature, the mixture is poured into ice and the product is extracted with dichloromethane. Washing with water, dilute hydrochloric acid and saturated sodium bicarbonate solution results in the crude product which is recrystallized from ether (0.31–8.02 g, about 82% yield). FAB-MS: M+H$^+$=454. NMR data consistent with Lemieux et al., *ACS Symp. Ser.* 39:90 (1976).

1-Thiophenyl-2-deoxy-2-phthalimido-β-D-glucopyranose [5]

Compound [2] (0.31–8.02 g, 0.68–17.7 mmol) is dissolved in 3.2–100 ml of dry dichloromethane, and thiophenol (0.15–3.9 g, 1.36–35.4 mmol) and tin tetrachloride (0.35–9.22 g, 1.36–35.4 mmol) are added and the mixture is stirred until reaction is complete. The reaction mixture is diluted and then washed with saturated sodium bicarbonate solution. The crude product compound [3] obtained in this way is purified by chromatography on silica gel with an ethyl acetate/isohexane gradient (0.27–7.14 g, 0.54–14.2 mmol, about 80%) and is dissolved in anhydrous methanol (3–90 ml) and catalytic amounts of sodium methylate (prepared from 0.002–0.05 g of sodium in 0.1–2 ml of methanol) are added. After the reaction is complete, the mixture is neutralized with an acidic ion exchanger (0.2–5 g Amberlite IR-120, H$^+$-form) compound [4] (0.21–5.31 g, 0.54–14.1 mmol, about 80% yield). FAB-MS: M+H$^+$=378. NMR data consistent with Nicolaou et al., *J. Am. Chem. Soc.* 112:3695 (1990)) and T. J. Caulfield, Ph.D. Dissertation, The University of Pennsylvania (1991).

1-Thiophenyl-3-O-allyl-6-O-benzyl-2-deoxy-2-phthalimido-β-D-glucopyranose [6]

The crude product compound [5] (0.21–5.31 g, 0.54–14.1 mmol) is stirred in anhydrous acetonitrile (3– 90 ml) with benzaldehyde dimethyl acetal (0.12–3.22 g, 0.81–21.1 mmol) and catalytic amounts of p-toluenesulfonic acid (4–90 mg) until the reaction is finished. The crude product resulting after washing with saturated sodium bicarbonate solution is taken up in anhydrous dimethylformamide (2.5–85 ml), and sodium hydride (0.02–0.51 g, 0.81–21.15 mmol) and allyl bromide (0.09–2.37 g, 0.75–19.74 mmol) are added. After the reaction is complete, methanol (0.06–1.55 ml, 2.7–70.5 mmol) is added, and the mixture is diluted with ethyl acetate and washed successively with saturated ammonium chloride and saturated sodium bicarbonate solution. The crude product compound [5] is purified by chromatography on silica gel with an ethyl acetate/isohexane gradient (0.23–5.98 g, 0.46–12.13 mmol, about 86%) and subsequently taken up in dry tetrahydrofuran (3.5–90 ml), and sodium cyanoborohydride (0.67–17.7 g, 10.8–282 mmol) is added. Subsequently, ethereal hydrochloric acid solution is slowly added until reaction is complete. After filtration, the organic phase is diluted with ethyl acetate and washed with saturated sodium bicarbonate solution to neutrality. The crude product compound [6] is purified by chromatography on silica gel with an ethyl acetate/isohexane gradient (0.17–4.56 g, 0.35–9.17 mmol, about 74% yield). FAB-MS: M+H$^+$=416. NMR data consistent with Nicolaou et al., *J. Am. Chem. Soc.* 112:3695 (1990) and T. J. Caulfield, Ph.D. Dissertation, The University of Pennsylvania (1991).

E10.1.2 Synthesis of the Galactose Unit [11].

1-Thiophenyl-2,3,4,6-tetra-O-acetylgalacto-β-D-pyranose [8]

Galactose [7] (0.18–3.6 g, 1–20 mmol) is suspended in dichloromethane (5–90 ml), and acetic anhydride (0.75–15.4 g, 7.5–150 mmol), triethylamine (0.8–16.3 g, 8–160 mmol) and catalytic amounts of dimethylaminopyridine (0.01–0.1 g) are added. After the reaction is complete, the mixture is poured into ice-water and the product is extracted with dichloromethane. The crude product obtained by washing the extract with dilute hydrochloric acid and saturated sodium bicarbonate solution is dissolved in dry dichloromethane (3.5–110 ml), and thiophenol (0.22–4.41 g, 2–40 mmol) and tin tetrachloride (0.51–10.28 g, 2–40 mmol) are added. After the reaction is complete, the mixture is diluted, and washing with saturated sodium bicarbonate solution results in the crude product compound [8] which is purified by chromatography on silica gel with an ethyl acetate/isohexane gradient (0.374–7.48 g, 0.85–17 mmol, about 85% yield). FAB-MS: M+H$^+$=441.NMR data consistent with Nicolaou et al., *J. Am. Chem. Soc.* 112:3695 (1990)); and T. J. Caulfield, Ph.D. Dissertation, The University of Pennsylvania (1991).

1-Thiophenyl-4,6-O-benzylidene-β-D-galactopyranose [9]

Compound [8] (0.374–7.48 g, 0.85–17 mmol) is dissolved in anhydrous methanol (4–150 ml), and catalytic amounts of sodium methylate (prepared from 0.003–0.06 g of sodium in 0.1–2.5 ml of methanol) are added. After the reaction is complete, the mixture is neutralized with an acidic ion exchanger (0.25–6 g Amberlite IR-120, H$^+$-form) and evaporated. The resulting reaction product is stirred in anhydrous acetonitrile (4.5–150 ml) with benzaldehyde dimethyl acetal (0.19–5.05 g, 1.27–33.1 mmol) and catalytic amounts of p-toluenesulfonic acid (4–90 mg) until the reaction is finished. Washing with saturated sodium bicarbonate solution results in the crude product compound [9] (0.28–5.51 g, 0.77–15.3 mmol, about 90% yield). FAB-MS: M+H$^+$=361. NMR data consistent with Nicolaou et al., *J. Am. Chem. Soc.* 114:3127 (1992) and C. W. Hummel, Ph.D. Dissertation, University of California, San Diego (1993).

1-Thiophenyl-2,3-di-O-acetyl-6-O-benzyl-β-D-galactopyranose [10]

Compound [9] (0.28–5.51 g, 0.77–15.3 mmol) is suspended in dichloromethane (4–60 ml), and acetic anhydride (0.23–4.75 g, 2–40 mmol), triethylamine (0.25–5.02 g, 2.46–49.23 mmol) and catalytic amounts of dimethylaminopyridine (0.01–0.08 g) are added. After the reaction is complete, the mixture is poured into ice-water and the product is extracted with dichloromethane. The crude product obtained by washing the extract with dilute hydrochloric acid and saturated sodium bicarbonate solution is dissolved in dry tetrahydrofuran (2.45–130 ml), and sodium cyanoborohydride (0.96–25.3 g, 15.4–402.8 mmol) is added. Subsequently ethereal hydrochloric acid solution is added slowly until the reaction is complete. After filtration, the organic phase is diluted with ethyl acetate and washed with saturated sodium bicarbonate solution to neutrality. The crude product compound [10] is purified by chromatography on silica gel with an ethyl acetate/isohexane gradient (0.27–5.46 g, 0.62–12.24 mmol, about 80% yield). FAB-MS: M+H$^+$=447. NMR data consistent with Nicolaou et al., *J. Am. Chem. Soc.* 114:3127 (1992)) and C. W. Hummel, Ph.D. Dissertation, University of California, San Diego (1993).

1-Fluoro-2,3,4-tri-O-acetyl-6-O-benzyl-β-D-galactopyranose [11]

Compound [9] (0.27–5.46 g, 0.62–12.24 mmol) is suspended in dichloromethane (4–60 ml) and acetic anhydride (0.14–2.91 g, 1.24–24.8 mmol), triethylamine (0.15–3.11 g, 1.53–30.53 mmol) and catalytic amounts of dimethylaminopyridine (0.003–0.04 g) are added. After the reaction is complete, the mixture is poured into ice-water and the product is extracted with dichloromethane. The crude product obtained by washing the extract with dilute hydrochloric acid and saturated sodium bicarbonate solution is taken up in dry dichloromethane (5–80 ml) and, at −78° C., dimethylaminosulfur trifluoride (0.25–4.89 g, 1.86–36.7 mmol) and N-bromosuccinimide (0.11–3.26 g, 0.93–18.36 mmol) are added, and the mixture is warmed to room temperature. After washing with saturated sodium bicarbonate solution, the mixture is concentrated and the byproducts of the reaction are removed by silica gel chromatography (stepwise gradient: ethyl acetate/isohexane) to produce compound [11] (0.21–4.14 g, 0.53–10.4 mmol, about 85% yield). FAB-MS: M+H$^+$=399. NMR data consistent with Nicolaou et al., *J. Am. Chem. Soc.* 114:3127 (1992) and C. W. Hummel, Ph.D. Dissertation, University of California, San Diego (1993).

E10.1.3 Synthesis of the Fucose Unit [17].

Fucose [15] (0.16–32.8 g, 1–20 mmol) is suspended in dichloromethane (5–90 ml), and acetic anhydride (0.75–15.43 g, 7.5–150 mmol), triethylamine (0.8–16.3 g, 8–160 mmol) and catalytic amounts of dimethylaminopyridine (0.01–0.1 g) are added. After the reaction is complete, the mixture is poured into ice-water and the product is extracted with dichloromethane. The crude product obtained by washing the extract with dilute hydrochloric acid and saturated sodium bicarbonate solution is dissolved in dry dichloromethane (3.5–110 ml) and thiophenol (0.22–4.41 g, 2–40 mmol) and tin tetrachloride (0.51–10.28 g, 2–40 mmol) are added. After the reaction is complete, the mixture is diluted, and washing with saturated sodium bicarbonate solution results in the crude product compound [16] which is purified by chromatography on silica gel with an ethyl acetate/isohexane gradient (0.34–6.88 g, 0.9–18 mmol, about 90% yield). FAB-MS: M+H$^+$=382. NMR data consistent with Nicolaou et al., *J. Am. Chem. Soc.* 114:3127 (1992) and C. W. Hummel, Ph.D. Dissertation, The University of California, San Diego (1993).

1-Thiophenyl-2,3,4-tri-O-benzyl-β-L-fucose [17]

Compound [16] (0.34–6.88 g, 0.9–18 mmol) is dissolved in anhydrous methanol (5–180 ml), and catalytic amounts of sodium methylate (prepared from 0.005–0.09 g of sodium in 0.2–2.9 ml of methanol) are added. After the reaction is complete, the mixture is neutralized with an acidic ion exchanger (0.3–6.7 g Amberlite IR-120, H$^+$-form) and evaporated. The resulting reaction product is taken up in anhydrous dimethylformamide (5–140 ml) and sodium hydride (0.16–3.21 g, 6.75–135 mmol) and benzyl bromide (0.92–18.46 g, 5.4–108 mmol) are added. After the reaction is complete, methanol (0.16–3.2 g, 5–100 mmol) is added, and the mixture is diluted with ethyl acetate and washed successively with saturated ammonium chloride and saturated sodium bicarbonate solutions. The crude product after chromatography on silica gel (ethyl acetate/isohexane gradient) is subsequently taken up in dry dichloromethane (8–120 mol) and, at −78° C., dimethylaminosulfur trifluoride (0.36–7.09 g, 2.69–53.18 mmol) and N-bromosuccinimide (0.16–4.73 g, 1.35–26.6 mmol) are added, and the mixture is warmed to room temperature. After washing with saturated sodium bicarbonate solution, the mixture is concentrated, and the byproducts of the reaction are removed by silica gel chromatography (stepwise gradient: ethyl acetate/isohexane) to result in compound [17] (0.33–6.47 g, 0.72–14.4 mmol, about 80% yield). FAB-MS: M+H$^+$=450. NMR data consistent with Nicolaou et al., *J. Am. Chem. Soc.* 114:3127 (1992) and C. W. Hummel, Ph.D. Dissertation, The University of California, San Diego (1993).

E10.1.4 Synthesis of the Neuraminic Acid Unit [22].

Methyl 5-acetamido-4,7,8,9-tetra-O-benzyl-2,3,5-trideoxy-2,3-dehydro-D-glycero-α-D-galacto-2-nonulopyranosylonate [21]

N-Acetylneuraminic acid [20] (0.31–6.18 g, 1–20 mmol) is added to acetic anhydride (3–100 ml), and catalytic amounts of sulfuric acid (0.001–0.5 g) are added. After the reaction is complete, the mixture is poured into ice-water and the crude product is extracted with ethyl acetate. The extracts are washed with saturated sodium bicarbonate solution and concentrated. The crude product is mixed with water and subsequently 1M sodium hydroxide solution is added. After the reaction is complete, the solvent is removed and the crude product is taken up in dimethylformamide (5–260 ml). Subsequently sodium hydroxide (0.03–7.2 g, 0.8–180 mmol), benzyl bromide (0.14–30.78 g, 0.8–180 mmol) and catalytic amounts of tetrabutylammonium iodide (0.005–0.75 g) are added, and the mixture is heated at 60° C. until the reaction is complete. Then methanol (1.5–35 ml) is added and the reaction mixture is adjusted to pH 2 by adding 1M aqueous hydrochloric acid. The crude product is obtained by extraction with ethyl acetate and washing of the extracts with saturated sodium bicarbonate solution. Purification of compound [21] takes place by chromatography on silica gel with a dichloromethane/methanol gradient (0.29–5.77 g, 0.45–9 mmol, yield about 45%). FAB-MS: M+H$^+$=642. NMR data consistent with Nicolaou et al., *J. Am. Chem. Soc.* 114:3127 (1992) and C. W. Hummel, Ph.D. Dissertation, University of California, San Diego (1993).

Chloromethyl 5-acetamido-4,7,8,9-tetra-O-benzyl-3,5-dideoxy-3-thiophenyl-D-glycero-α-D-galacto-2-nonulopyranosylonate [22]

Compound [21] (0.29–5.77 g, 0.45–9 mmol) is taken up in dichloromethane (2.5–80 ml) and phenylsulfenyl chloride is added. After the reaction is complete, the mixture is washed with saturated sodium bicarbonate solution and concentrated. The crude product compound [22] is purified by chromatography on silica gel with an ethyl acetate/isohexane gradient (0.29–5.83 g, 0.36–7.2 mmol, about 80% yield). FAB-MS: M+H⁺=810. NMR data consistent with Nicolaou et al., *J. Am. Chem. Soc.* 114:3127 (1992) and C. W. Hummel, Ph.D. Dissertation, University of California, San Diego (1993).

E10.2 Assembly of the Disaccharide from the N-acetylglucosamine Unit and the Galactose Unit.

1-Thiophenyl-(2,3,4-tri-O-acetyl-6-O-benzyl-β-D-galactopyranosyl)-(1-4)-3-O-alkyl-2-deoxy-2-acetamido-β-D-glucopyranose [12]

The N-acetylglucosamine derivative [5] (0.17–4.56 g, 0.35–9.17 mmol) and the galactose derivative [11] (0.21–4.14 g, 0.53–10.4 mmol) are dissolved in dichloromethane (3–120 ml) and, at 0° C., 4 Å molecular sieves (0.15–7.8 g), silver perchlorate (0.11–5.39, 0.525–26 mmol) and tin(II) chloride (0.1–4.93 g, 0.525–26 mmol) are added. After the reaction is complete, the mixture is filtered and washed with saturated sodium bicarbonate solution. The crude product compound [12] is purified by chromatography on silica gel with an ethyl acetate/isohexane gradient (0.23–5.61 g, 0.26–6.42 mmol, about 70% yield). FAB-MS: M+H⁺=874. NMR data consistent with Nicolaou et al., *J. Am. Chem. Soc.* 114:3127 (1992) and C. W. Hummel, Ph.D. Dissertation, University of California, San Diego (1993).

1-Thiophenyl-(2,3,4-tri-O-acetyl-6-O-benzyl-β-D-galactopyranosyl)-(1-4)-2-deoxy-2-acetamido-β-D-glucopyranose [13]

Compound [12] (0.23–5.61 g, 0.26–6.42 mmol) is dissolved in ethanol (3–90 ml) and heated at 95° C. with catalytic amounts of tetrakis(triphenylphosphine)-ruthenium(II) hydride (0.005–0.04 g). After the reaction is complete, the mixture is filtered, concentrated and taken up in methanol (2.5–85 ml) and catalytic amounts of p-toluenesulfonic acid (0.001–0.08 g) are added. After the reaction is complete, the mixture is washed with saturated sodium bicarbonate solution and, after concentration, the crude product compound [13] is obtained. Purification takes place by chromatography on silica gel with an ethyl acetate/isohexane gradient (0.2–4.8 g, 0.234–5.78 mmol, about 90% yield). FAB-MS: M+H⁺=834. NMR data consistent with Nicolaou et al., *J. Am. Chem. Soc.* 114:3127 (1992) and C. W. Hummel, Ph.D. Dissertation, University of California, San Diego (1993).

E10.3 Assembly of the Trisaccharide from the Disaccharide and the Fucose Unit.

1-Thiophenyl-(2,3,4-tri-O-acetyl-6-O-benzyl-β-D-galactopyranosyl)-(1-4)-[(2,3,4-tri-O-benzyl-α-L-fucopyranosyl)-(1-3)]-2-deoxy-2-acetamido-β-D-glucopyranose [18]

Compound [13] (0.2–4.81 g, 0.234–5.78 mmol) is dissolved with compound [17] (0.17–4.15 g, 0.37–9.25 mmol) in dry diethyl ether (5–100 ml) and stirred with 4 Å molecular sieves (0.1–6.8 g), silver perchlorate (0.15–3.59 g 0.702–17.34 mmol) and tin(II) chloride (0.13–3.29 g, 0.702–17.34 mmol) until the reaction is complete. The mixture is subsequently filtered, and the crude product compound [18] obtained after concentration is purified by chromatography on silica gel with an ethyl acetate/isohexane gradient (0.25–6.2 g, 0.2–4.91 mmol, about 85% yield). FAB-MS: M+H⁺=1262. NMR data consistent with Nicolaou et al., *J. Am. Chem. Soc.* 114:3127 (1992) and C. W. Hummel, Ph.D. Dissertation, University of California, San Diego (1993).

E10.4 Assembly of the Tetrasaccharides from the Trisaccharide and the N-acetylglucosamine Unit.

1-(o-Nitrobenzyl)-(6-O-benzyl-β-D-galactopyranosyl)-(1-4)-[(2,3,4-tri-O-benzyl-α-L-fucopyranosyl)-(1-3)-2-deoxy-2-acetamido-β-D-glucopyranose [23]

Compound [18] (0.25–6.2 g, 0.2–4.91 mmol) is taken up in dry dichloromethane (3–85 ml) and, at −78° C., dimethylaminosulfur trifluoride (0.08–1.93 g, 0.6–14.73 mmol) and N-bromosuccinimide (0.05–1.23 g, 0.28–6.87 mmol) are added, and the mixture is warmed to room temperature. After washing with saturated sodium bicarbonate solution, the mixture is concentrated and the byproducts of the reaction are removed by silica gel chromatography (stepwise gradient: ethyl acetate/isohexane) giving compound [22] (0.33–6.47 g, 0.72–14.4 mmol, about 80% yield). The reaction product is dissolved in dichloromethane and, at −78° C., o-nitrobenzyl alcohol (0.08–1.88 g, 0.5–12.28 mmol), 4 Å molecular sieves (0.1–7.5 g), silver trifluoromethanesulfonate (0.18–4.42 g, 0.7–17.19 mmol) and hafnocene dichloride (0.27–6.53 g, 0.7–17.19 mmol) are added, and the mixture is allowed to warm to room temperature. Filtration is followed by washing with saturated sodium bicarbonate solution and concentration. The crude product obtained in this way is purified by chromatography on silica gel (dichloromethane/methanol gradient) and dissolved in dry methanol (3–80 ml), and catalytic amounts of sodium methylate (prepared from 0.001–0.09 g of sodium methylate (prepared from 0.001–0.09 g of sodium in 0.2–2.5 ml of methanol) are added. After the reaction is complete, the mixture is neutralized with an acidic ion exchanger (0.2–6.5 g Amberlite IR-120, H⁺-form). Evaporation results in compound [23]. FAB-MS: M+H⁺=1186. NMR data consistent with Nicolaou et al., *J. Am. Chem. Soc.* 114:3127 (1992) and C. W. Hummel, Ph.D. Dissertation, University of California, San Diego (1993).

1-(O-N-Nitrobenzyl)-[(methyl-5-acetamido-4,7,8,9-tetra-O-benzyl-3,5-dideoxy-D-glycero-α-D-galacto-2-nonulopyranosylonatyl)-(2-3)-(6-O-benzyl-β-D-galactopyranosyl)-(1-4)]-(2,3,4-tri-O-benzyl-α-L-fucopyranosyl)-(1-3)]-2-deoxy-2-acetamido-β-D-glucopyranose [24]

The resulting reaction product compound [23] is dissolved with compound [22] (0.1–2.81 g, 0.12–3.47 mmol) in tetrachloromethane and, at 0° C., 4 Å molecular sieves (0.08–0.7 g), mercury(II) cyanide (0.13–2.67 g, 0.36–10.43 mmol) and mercury(II) bromide (0.14–1.25 g, 0.12–3.47 mmol) are added, and the mixture is slowly warmed to room temperature. After washing with saturated sodium bicarbonate solution, the mixture is concentrated and the crude product [24] is purified by chromatography on silica gel with an ethyl acetate/isohexane gradient (0.14–3.36 g, 0.07–1.72 mmol, about 35% yield). FAB-MS: M+H⁺=1959. NMR data consistent with Nicolaou et al., *J. Am. Chem. Soc.* 114:3127 (1992) and C. W. Hummel, Ph.D. Dissertation, University of California, San Diego (1993).

1-Fluoro-[(methyl-5-acetamido-4,7,8,9-tetra-O-benzyl-3,5-dideoxy-D-glucero-α-D-galacto-2-nonulopyranosylonatyl)-(2-3)-(6-O-benzyl-2,4-di-O-acetyl-β-D-galactopyranosyl)-(1-4)-(2,3,4-tri-O-benzyl-α-L-fucopyranosyl)-(1-3)-2-deoxy-2-acetamido-β-D-glucopyranose Compound [24] (0.14–3.36 g, 0.07–1.72 mmol) is dissolved in acetic anhydride (0.5–10 ml) and pyridine (0.5–10 ml), and catalytic amounts of dimethylaminopyridine (0.001–0.1 g) are added. After the reaction is complete, the mixture is poured into ice-water and the crude product is extracted with ethyl acetate. The solution is subsequently washed successively with dilute hydrochloric acid and saturated sodium bicarbonate solution. The reaction product is taken up in a 10:1 tetrahydrofuran/water mixture (0.5–30 ml) and irradiated at 0° C. with a UV lamp. After the reaction is complete, the mixture is concentrated, taken up in toluene (0.5–60 ml) and heated under reflux with triphenyltin hydride (0.25–6.04 g; 0.7–17.2 mmol) and azoisobutyronitrile (0.01–0.25 g, 0.06–1.55 mmol). After the reaction is complete, the mixture is concentrated and the reaction product is chromatographed on silica gel with a dichloromethane/methanol gradient (0.036–0.92 g, 0.02–0.52 mmol, about 30% yield). FAB-MS: M+H$^+$=1644. NMR data consistent with Nicolaou et al., *J. Am. Chem. Soc.* 114:3127 (1992) and C. W. Hummel, Ph.D. Dissertation, University of California, San Diego (1993).

The purified product is dissolved in dry dichloromethane (0.1–10 ml) and, at −78° C., diethylaminosulfur trifluoride (0.016–0.41 g, 0.12–3.1 mmol) is added. After the reaction is complete, the mixture is extracted with saturated sodium bicarbonate solution to result, after concentration, in the crude product compound [25] which is purified by chromatography on silica gel with a dichloromethane/methanol gradient.

1-(6-Aminohexyl)-O-[(methyl-5-acetamido-3,5
-dideoxy-D-glycero-α-galacto-2
-nonulopyranosylonatyl)-(2-3)-(-β-D-galactopyranosyl)-(1-4)-(α-L-fucopyranosyl)-(1
-3)-2-deoxy-2-acetamido-β-D-glucopyranose [26]

Compound [25] and 6-azidohexanol (0.017–0.44 g, 0.12–3.1 mmol) are dissolved in dry acetonitrile and, at 0° C., 4 Å molecular sieves (0.06–1.5 g) and trimethylsilyl trifluoromethanesulfonate (0.001–1.4 g, 0.005–5.1 mmol) are added. After the reaction is complete, the mixture is filtered and washed with saturated sodium bicarbonate solution. Concentration results in the crude product which is purified by chromatography on silica gel with an ethyl acetate/isohexane gradient (0.021–0.51 g, 0.01–0.27 mmol, about 55% yield). It is subsequently taken up in methanol/hydrazine hydrate (1:1) (1–30 ml) and heated at 80° C. until reaction is complete. After evaporation of the solvent, the crude product is taken up in dichloromethane/methanol (1:1) and stirred at 0° C. with acetic anhydride (0.03–4.1 mmol) until the reaction is complete. Evaporation is followed by reduction of the azide with hydrogen in the presence of catalytic amounts of palladium on carbon (10%) (0.001–0.15 g) in methanol (1–45 ml). The crude product compound [26] obtained after evaporation is purified by gel chromatography on Biogel P2 (0.0064–0.17 g, 0.007–0.18 mmol, about 65% yield). FAB-MS: M+H$^+$=920. $^1$H-NMR [300 MHz, D$_2$O]: 4.92 (Fuc-H-1), 4.36 (GlcNAc-H-1), 4.28 (Gal-H-1), 4.1–3.35 (m), 3.29 (CH$_2$ —NH$_3^+$OAc$^-$), 2.19 (NANA-H-3eq.), 1.93 (NANA-NCOCH$_3$), 1.81 (GlcNCOCH$_3$), 1.77 (NANA-H-3ax.), 1.58–1.18 (O—(CH$_2$)$_5$—CH$_2$—NH$_3^+$OAc$^-$), 0.99 (Fuc-CH$_3$) ppm.

E10.5 Reaction of the Polymer/Potentiator Complex with the Carbohydrate/Spacer on the Other Hand to Form Covalent Bonds.

Poly-D,L-succinimide-co-aspartamido-C$_6$-GlcNAc
(degree of loading: 12%)
(=Poly-D,L-succinimide-co-α,β-D,L-aspartamido-
6-hexyl-2-deoxy-2-acetamido-β-D-glucopyranose)

PSI (1 g, 10.3 μmol, Mw: 24,200) is introduced into DMF (=dimethylformamide, 4 ml, dried and distilled), and 1-(6-aminohexyl)-2-deoxy-2-acetamido-β-D-glucopyranose (H$_2$N—C$_6$-GlcNAc) (0.45 g, 1.41 mmol) in 4 ml of DMF is added. The mixture is stirred under N$_2$ at room temperature for 4 h. It is then precipitated with 80 ml of 1-butanol, and the resulting polymer is washed with methanol. After a second precipitation from DMF in 1-butanol, the product is again washed with methanol and subsequently dried under oil pump vacuum. Yield is 1.2 g (86%). Degree of substitution according to NMR is 12%.

PHEA-co-aspartamido-C$_6$-GlcNAc (degree of
loading: 12%)
(=Poly-α,β-(2-hydroxyethyl)-D,L-aspartamide-co-α,
β-D,L-aspartamido-6-hexyl-2-deoxy-2-acetamido-β-
D-glucopyranose)

PSI-co-aspartamido-C$_6$-GlcNAc as prepared above (0.8 g, 5.9 μmol) is dissolved in 6 ml of DMF, and freshly distilled hydroxyethylamine (325 mg, 5.4 mmol) is added. After stirring at room temperature under N$_2$ for 4 h, the mixture is precipitated in monobutanol. The resulting white flocculent polymer is washed with methanol, dissolved in H$_2$O and freeze-dried. After the second precipitation from the DMF/H$_2$O (15:1) in 1-butanol, the product is again washed with methanol and freeze-dried from H$_2$O. Yield is 1 g (90%). Degree of substitution according to NMR is 12% H$_2$N-C$_6$-GlcNAc, 88% HEA $^1$H-NMR (300 MHz, D$_2$O): 1.3 (—(CH$_2$)$_2$—), 1.5 (—CH$_2$—Ch$_2$—NHCO— and —CH$_2$—CH$_2$—O—GlcNAc), 2.04 (GlcNCOCH$_3$), 2.8 (Asp. —CH$_2$—CO), 3.35 (—CONH—CH$_2$—CH$_2$—OH), 3.65 (—CONH—CH$_2$—CH$_2$—OH), 4.5 (GlcNAc-H-1), 4.7 (Asp. —CH(NH—)—CO).

Poly-succinimide-co-HEA-co-aspartamido-C$_6$-GlcNAc
(degree of loading: 12%)
(=Poly-D,L-succinimide-co-α,β-(2
-hydroxyethyl)-D,L-aspartamide-co-D,L-aspartamido-
6-hexyl-2-deoxy-2
-acetamido-β-D-glucopyranose)

PSI-co-aspartamido-C$_6$-GlcNAc as prepared above (0.4 g, 3 μmol) and hydroxyethylamine (0.1 g, 1.6 mmol) are reacted in analogy to the synthesis of PHEA-co-aspartamido-C$_6$-GlcNAc above. Yield is 380 mg (78%) and degree of substitution according to NMR is 53% HEA, 12% H$_2$N-C$_6$-GlcNAc.

Poly-succinimide-co-aspartamido-C$_6$-GlcNAc
(degree of loading: 22%)
(=Poly-D,L-succinimide-co-α,β
-D,L-aspartamido-6-hexyl-2-deoxy-2-acetamido-β-
D-glucopyranose)

PSI-co-aspartamido-C$_6$-GlcNAc as prepared above (0.32 g, 3.3 mmol) is reacted with 0.3 g (1.0 mmol) of H$_2$N-C$_6$-GlcNAc and worked up by precipitation. Yield is 400 mg (72%) and degree of substitution according to NMR is 22%.

Poly-succinimide-co-HEA-co-aspartamido-C$_6$-GlcNAc
(degree of loading: 22%)
(=Poly-D,L-succinimide-co-α,β-(2-hydroxyethyl)-
D,L-aspartamide-co-D,L-aspartamido-6-hexyl-2-
deoxy-2-acetamido-β-D-glucopyranose)

PSI-co-aspartamido-C$_6$GlcNAc from Example 8 (0.4 g, 2.39 mmol) and hydroxyethylamine (0.1 g, 1.67 mmol) are reacted in analogy to the synthesis of PHEA-co-aspartamido-C$_6$-GlcNAc above. Yield is 410 mg (84%) and degree of substitution according to NMR is 22% 4, 60% HEA.

Poly-HEA-co-3-dimethylamino-1-propylamidoaspartamide-co-aspartamido-$C_6$-GlcNAc (degree of loading: 12%)
(=Poly-α,β-(2-hydroxyethyl)-D,L-aspartamide-co-α,β-(3-dimethylamino-1-propylamido-D,L-aspartamide-co-D,L-aspartamido-6-hexyl-2-deoxy-2-acetamido-β-D-glucopyranose)

PSI (0.1 g, 1.0 μmol) is dissolved in 1 ml of DMF, and $H_2N$-$C_6$-GlcNAc (45 mg, 0.14 mmol) and hydroxyethylamine (12 mg, 0.2 mmol) are added. After 3 h at 35° C., freshly distilled 3-dimethylamino-1-propylamine (105 mg, 0.1 mmol) and, after a further 3 h at 35° C., hydroxyethylamine (37 mg, 0.6 mmol) are added. The mixture is stirred for 3 h and worked up in analogy to the synthesis of PHEA-co-aspartamido-$C_6$-GlcNAc above. Yield is 160 mg (82%) and degree of substitution according to NMR is 78% HEA, 10% dimethylaminopropylamine, 12% $H_2N$-$C_6$-GlcNAc.

Poly-HEA-co-4-aminobutyl-1-amidoaspartamide-co-aspartamido-$C_6$-GlcNAc (degree of loading: 12%)
(=Poly-α,β-(2-hydroxyethyl)-D,L-aspartamide-co-α,β-4-aminobutyl-1-amido-D,L-aspartamide-co-D,L-aspartamido-6-hexyl-2-deoxy-2-acetamido-β-D-glucopyranose)

PSI (0.75 g, 7.7 μmol) is dissolved in dried and distilled DMF (150 ml), and 1,4-diaminobutane (34 mg, 0.39 mmol) is added and the mixture is stirred at room temperature for 2 days. It is concentrated to about 1 ml under oil pump vacuum, $H_2N$-$C_6$-GlcNAc (34 mg, 1.1 mmol) is added and the mixture is stirred at 35° C. for 3 h. After addition of hydroxyethylamine (0.47 g, 7.7 mmol) the mixture is stirred at 35° C. for a further 3 h and subsequently worked up in analogy to the synthesis of PHEA-co-aspartamido-$C_6$-GlcNAc above. Yield is 100 mg (70%) and degree of substitution according to NMR is 83% HEA, 12% $H_2N$-$C_6$-GlcNAc, 5% diaminobutane.

Poly-HEA-co-aspartamido-$C_6$-LacNAc
(=Poly-α,β-(2-hydroxyethyl)-D,L-aspartamide-co-D,L-aspartamido-6-hexyl-O-(β-D-galactopyranosyl)-(1-4)-2-deoxy-2-acetamido-β-D-glycopyranose)

PSI (70 mg, 0.72 μmol) is dissolved in 0.5 ml of DMF, and a solution of hydroxyethylamine (9 mg, 0.147 mmol) and $H_2N$-$C_6$-LacNAc (41 mg, 0.086 mmol) in 0.5 ml of DMF/NMP (10:1) is added and the mixture is stirred at 35° C. for 6 h. After addition of hydroxyethylamine (35 mg, 0.58 mmol), the mixture is stirred for a further 3 h. Working up is carried out in analogy to the synthesis of PHEA-co-aspartamido-$C_6$-GlcNAc above. Yield is 90 mg (66%) and degree of substitution according to NMR is 93% HEA, 7% $H_2N$-$C_6$-LacNAc $^1$H-NMR (300 MHz, $D_6$DMSO): 1.2 (—($CH_2$)$_2$—), 1.4 (—$CH_2$—$CH_2$—NHCO— and —$CH_2$—$CH_2$—O—LacNAc), 1.80 (GlcNCOCH$_3$), 3.15 (—CONH—$CH_2$—$CH_2$—OH), 4.2 (Gal-H-1), 4.3 (GlcNAc-H-1), 4.7 (Asp. —CH(NH)—CO).

Poly-HEA-co-aspartamido-$C_6$-sialyl Lewis X
(=Poly-α,β-(2-hydroxyethyl)-D,L-aspartamide-co-D,L-aspartamido-6-hexyl-O-[(methyl-5-acetamido-3,5-dideoxy-D-glycero-α-D-galacto-2-nonulopyranosylonatyl)-(2-3)-(β-D-galactopyranosyl)-(1-4)]-(α-L-fucopyranosyl)-(1-3)-2-deoxy-2-acetamido-β-D-glucopyranose)

PSI (70 mg, 0.72 μmol) is dissolved in 0.5 ml of DMSO, hydroxyethylamine (18 mg, 0.3 mmol) is added and the mixture is stirred at 35° C. for 2 h. Compound [26] (46 mg, 0.05 mmol) is dissolved with triethylamine (5 mg) in 0.2 ml of $H_2O$, added to the polymer mixture and stirred at 35° C. for 6 h. The mixture is then left to react with the addition of $H_2O$ and with additional hydroxylamine (27 mg, 0.45 mmol) for a further 4 h. Working up is carried out in analogy to the synthesis of PHEA-co-aspartamido-$C_6$-GlcNAc above. Yield is 92 mg (64%) and degree of substitution according to NMR is 95% HEA, 5% compound [26].

Poly-L-lysine-(2-hydroxyethyl)amide-co-L-lysinamido-$C_6$-GlcNAc-fumaramide (degree of loading: 13%)
(=Poly-L-lysine-(2-hydroxyethyl)-amide-co-L-lysinamido-6-hexyl-2-deoxy-2-acetamido-β-D-glucopyranose-fumaramide)

Poly-L-lysine methyl ester fumaramide (240 mg, 1 μmol) is dissolved in 5 ml of DMSO at 80° C. After cooling to room temperature, $H_2N$-$C_6$-GlcNAc (48 mg, 0.15 mmol) is added, and the mixture is stirred at 35° C. for 4 h. Hydroxyethylamine (101 mg, 1 mmol) is added and the mixture is stirred at room temperature for a further 3 h. The working up comprises precipitation twice in acetone and freeze-drying from $H_2O$. Yield is 166 mg (55%) and degree of substitution according to NMR is 87% HEA, 13% $H_2N$-$C_6$-GlcNAc.

It will be apparent to those skilled in the art that various modifications and variations can be made to the compositions of matter and methods of this invention. Thus, it is intended that the present invention cover the modifications and variations of this invention provided they come within the scope of the appended claims and their equivalents.

Express Incorporation by Reference

Each of the publications cited in this specification is hereby expressly incorporated herein, in its entirety, by reference. Additionally, the complete specifications of German Patent Application P 42 41 829.1, filed 11 Dec. 1992, and P 43 26 777.7, filed 10 Aug. 1993, are expressly incorporated herein by reference.

What is claimed is:

1. A carbohydrate-containing polymer comprising:
  (i) a hydrophilic polymer selected from the group consisting of poly-D,L-succinimide, poly-α,β-(2-hydroxyethyl)-D,L-aspartamide, poly-D,L-succinimide-poly-α,β-(2-hydroxyethyl)-D,L-aspartamide copolymer, poly-L-lysine methyl ester-fumaramide, polyglutamate, and hydroxyethylstarch;
  (ii) a carbohydrate selected from the group consisting of N-acetylglucosamine, sialyl-Lewis X and sialyl-Lewis A; and
  (iii) a bifunctional spacer linking said carbohydrate to said hydrophilic polymer.

2. A carbohydrate-containing polymer according to claim 1, wherein said bifunctional spacer is selected from (i) a 6-aminohexanol-based spacer and (ii) and N-(6'-hydroxyhexyl)-6-aminohexanoamide-based spacer, whereby the amino group of said spacer is linked to said polymer via an amide bond, and the hydroxyl group of said spacer is linked to said carbohydrate via a glycosidic bond.

3. A carbohydrate-containing polymer according to claim 2, wherein said hydrophilic polymer is poly-D,L-succinimide, and said carbohydrate is N-acetylglucosamine.

4. A carbohydrate-containing polymer according to claim 3, wherein said polymer consists of poly-D,L-succinimide-co-α,β-D,L-aspartamido-6-hexyl-2-deoxy-2-acetamido-β-D-glucopyranose.

5. A carbohydrate-containing polymer according to claim 2, further comprising a potentiator.

6. A carbohydrate-containing polymer according to claim 5, wherein said potentiator is a 2-aminoethanol-based potentiator, whereby said 2-aminoethanol-based potentiator is linked to said polymer via an amide linkage.

7. A carbohydrate-containing polymer according to claim 6, wherein said carbohydrate is N-acetyl glucosamine.

8. A carbohydrate-containing polymer according to claim 7, wherein said hydrophilic polymer is poly-D,L-succinimide.

9. A carbohydrate-containing polymer according to claim 7, wherein said carbohydrate-containing polymer consists of poly-α,β-(2-hydroxyethyl)-D,L-aspartamide-co-α,β-D,L-aspartamido-6 -hexyl-2-deoxy-2-acetamido-β-D-glucopyranose.

10. A carbohydrate-containing polymer according to claim 6, wherein said hydrophilic polymer is poly-D,L-succinimide, and said carbohydrate is sialyl Lewis X.

11. A carbohydrate-containing polymer according to claim 10, wherein said carbohydrate-containing polymer consists of poly-α,β-(2-hydroxyethyl)-D,L-aspartamide-co-D,L-aspartamido-6 -hexyl-O-[(methyl-5-acetamido-3,5-dideoxy-D-glycero-α-D-galacto-2-nonulopyranosylonatyl)-(2-3)-(β-D-galactopyranosyl)-(1-4)-(α-L-fucopyranosyl)-(1-3)-2-deoxy-2-acetamido-β-D-glucopyranose.

12. A carbohydrate-containing polymer according to claim 7, wherein said hydrophilic polymer is poly-L-lysine methyl ester-fumaramide.

13. A carbohydrate-containing polymer according to claim 12, wherein said carbohydrate-containing polymer consists of poly-L-lysine-(2-hydroxyethyl)-amide-co-L-lysinamido-6 -hexyl-2-deoxy-2-acetamido-β-D-glucopyranosefumaramide.

14. A pharmaceutical composition comprising a compound according to claim 1.

* * * * *